US008647588B2

(12) United States Patent
Recknor et al.

(10) Patent No.: US 8,647,588 B2
(45) Date of Patent: Feb. 11, 2014

(54) TIP TRAY ASSEMBLY FOR OPTICAL SENSORS

(75) Inventors: Michael W. Recknor, Oakland, CA (US); Hong Tan, San Jose, CA (US); Robert Zuk, Atherton, CA (US); Krista Leah Witte, Hayward, CA (US); Sae Choo, Sunnyvale, CA (US); Scott Lockard, Los Gatos, CA (US)

(73) Assignee: Pall Corporation, Port Washington, NY (US)

( * ) Notice: Subject to any disclaimer, the term of this patent is extended or adjusted under 35 U.S.C. 154(b) by 203 days.

(21) Appl. No.: 13/101,112

(22) Filed: May 4, 2011

(65) Prior Publication Data

US 2011/0268610 A1 Nov. 3, 2011

Related U.S. Application Data

(62) Division of application No. 11/423,669, filed on Jun. 12, 2006, now abandoned.

(60) Provisional application No. 60/690,325, filed on Jun. 13, 2005.

(51) Int. Cl.
*G01N 21/75* (2006.01)
*B01L 3/00* (2006.01)
*C12Q 1/68* (2006.01)

(52) U.S. Cl.
USPC ............. 422/407; 422/50; 422/400; 422/401; 422/408; 422/417; 422/503; 422/504; 422/511; 422/521

(58) Field of Classification Search
USPC ........... 422/50, 400, 401, 407, 408, 503, 504, 422/511, 521
See application file for complete search history.

(56) References Cited

U.S. PATENT DOCUMENTS

| 4,830,451 A | 5/1989 | Stone |
| 5,296,347 A | 3/1994 | LaMotte, III |

(Continued)

FOREIGN PATENT DOCUMENTS

| EP | 2026060 A1 | 2/2009 |
| GB | 2084317 A | 4/1982 |

(Continued)

OTHER PUBLICATIONS

Boiarski, A. et al., "Integrated-Optic Biosensor", SPIE, Fiber Optic Sensors in Medical Diagnostics, vol. 1886, 1993, pp. 15-26.

(Continued)

*Primary Examiner* — Dean Kwak
(74) *Attorney, Agent, or Firm* — Leydig, Voit & Mayer, Ltd.

(57) ABSTRACT

An apparatus and method for packaging of an optical sensing fiber is disclosed. The apparatus includes a substrate with a plurality of openings, and each opening is configured for holding an optical sensing assembly. The assembly is positioned in the opening with a tip of the assembly extending through the opening to be suspended from the substrate. In addition, openings are arranged so the assembly positioned therein avoids contacting another assembly positioned therein. The apparatus can include a support member for supporting the substrate and positioning the substrate so the tip of the assembly suspended from the opening in the substrate contacts solution in one of a plurality of wells in a container adjacent to the substrate. The assembly can be configured for preparing of the optical assembly for assay. An agitation assembly for agitating the container to create flow of the solution in the container wells over an optical sensing assembly is also disclosed.

19 Claims, 13 Drawing Sheets

(56) References Cited

U.S. PATENT DOCUMENTS

| | | | |
|---|---|---|---|
| 5,301,001 A | 4/1994 | Murphy et al. | |
| 5,359,405 A | 10/1994 | Andrews | |
| 5,422,970 A | 6/1995 | Miller et al. | |
| 5,425,039 A | 6/1995 | Hsu et al. | |
| 5,452,087 A | 9/1995 | Taylor et al. | |
| 5,528,367 A | 6/1996 | Putnam et al. | |
| 5,561,069 A | 10/1996 | Brigham-Burke et al. | |
| 5,594,819 A | 1/1997 | Narendran et al. | |
| 5,606,170 A | 2/1997 | Saaski et al. | |
| 5,629,214 A | 5/1997 | Crosby | |
| 5,631,171 A | 5/1997 | Sandstrom et al. | |
| 5,647,038 A | 7/1997 | Minden et al. | |
| 5,682,237 A | 10/1997 | Belk | |
| 5,701,193 A | 12/1997 | Vogel et al. | |
| 5,732,169 A | 3/1998 | Riant et al. | |
| 5,753,518 A | 5/1998 | Karlsson | |
| 5,804,453 A | 9/1998 | Chen | |
| 5,869,835 A | 2/1999 | Udd | |
| H1813 H | 11/1999 | Kersey | |
| 5,982,959 A | 11/1999 | Hopenfeld | |
| 6,055,080 A | 4/2000 | Furstenau et al. | |
| 6,078,706 A | 6/2000 | Nau et al. | |
| 6,139,797 A | 10/2000 | Suzuki et al. | |
| 6,143,574 A | 11/2000 | Karlsson et al. | |
| 6,241,397 B1 | 6/2001 | Bao et al. | |
| 6,244,214 B1 | 6/2001 | Hebrank | |
| 6,248,539 B1 | 6/2001 | Ghadiri et al. | |
| 6,254,830 B1 | 7/2001 | Pivarnik et al. | |
| 6,275,628 B1 | 8/2001 | Jones et al. | |
| 6,277,651 B1 | 8/2001 | Groger et al. | |
| 6,281,976 B1 | 8/2001 | Taylor et al. | |
| 6,436,351 B1 * | 8/2002 | Gubernator et al. | 422/553 |
| 6,445,838 B1 | 9/2002 | Caracci et al. | |
| 6,496,618 B1 | 12/2002 | Fernando et al. | |
| 6,539,136 B1 | 3/2003 | Dianov et al. | |
| 6,571,639 B1 | 6/2003 | May et al. | |
| 6,590,665 B2 | 7/2003 | Painchaud et al. | |
| 6,611,334 B1 | 8/2003 | Fernando et al. | |
| 6,661,520 B1 | 12/2003 | Lin et al. | |
| 6,671,055 B1 | 12/2003 | Wavering et al. | |
| 6,687,011 B1 | 2/2004 | Lee et al. | |
| 6,720,177 B2 | 4/2004 | Ghadiri et al. | |
| 6,744,939 B2 | 6/2004 | Lampert et al. | |
| 6,838,051 B2 * | 1/2005 | Marquiss et al. | 422/63 |
| 6,870,624 B2 | 3/2005 | Hobbs et al. | |
| 6,870,630 B2 | 3/2005 | Budach et al. | |
| 7,158,225 B2 | 1/2007 | Tedesco et al. | |
| 7,319,525 B2 | 1/2008 | Tan et al. | |
| 7,394,547 B2 | 7/2008 | Tan et al. | |
| 7,445,887 B2 | 11/2008 | Zuk et al. | |
| 7,656,536 B2 | 2/2010 | Tan et al. | |
| 7,728,982 B2 | 6/2010 | Tan et al. | |
| 7,838,301 B2 * | 11/2010 | Muraishi | 436/164 |
| 2001/0048072 A1 | 12/2001 | Painchaud et al. | |
| 2002/0127565 A1 | 9/2002 | Cunningham et al. | |
| 2003/0026735 A1 | 2/2003 | Nolte et al. | |
| 2003/0112443 A1 | 6/2003 | Hjelme et al. | |
| 2003/0215791 A1 | 11/2003 | Garini et al. | |
| 2003/0224397 A1 | 12/2003 | Lowman et al. | |
| 2004/0022475 A1 | 2/2004 | Pennington | |
| 2004/0091397 A1 * | 5/2004 | Picard | 422/99 |
| 2004/0151626 A1 | 8/2004 | Cunningham et al. | |
| 2004/0186359 A1 | 9/2004 | Beaudoin et al. | |
| 2005/0176155 A1 * | 8/2005 | Klein et al. | 436/163 |
| 2005/0254062 A1 | 11/2005 | Tan et al. | |
| 2006/0050358 A1 | 3/2006 | Bigman | |
| 2007/0070356 A1 | 3/2007 | Tan et al. | |
| 2007/0161042 A1 | 7/2007 | Zuk et al. | |
| 2009/0068694 A1 | 3/2009 | Zuk et al. | |
| 2009/0252649 A1 * | 10/2009 | Nomura | 422/52 |
| 2010/0093106 A1 | 4/2010 | Witte et al. | |

FOREIGN PATENT DOCUMENTS

| | | |
|---|---|---|
| JP | 01039555 A | 2/1989 |
| JP | 11064338 A | 3/1999 |
| JP | 2000-98182 A | 4/2000 |
| JP | 2007-510907 A | 4/2007 |
| SG | 133108 | 4/2008 |
| SG | 122203 | 3/2009 |
| WO | WO 92/16826 A1 | 10/1992 |
| WO | WO 97/18472 A1 | 5/1997 |
| WO | WO 2004/025282 A1 | 3/2004 |
| WO | WO 2005/047854 A2 | 5/2005 |
| WO | WO 2006/074444 A2 | 7/2006 |
| WO | WO 2006/138294 A2 | 12/2006 |
| WO | WO 2007/081520 A2 | 7/2007 |
| WO | WO 2008/033535 A2 | 3/2008 |

OTHER PUBLICATIONS

Brecht, A. et al., "Direct Monitoring of Antigen-Antibody Interactions by Spectral Interferometry", Sensors and Actuators, vol. B5, 1992, pp. 96-100.

Brecht, A. et al., "Interferometric Immunoassay in a FIA-System: a Sensitive and Rapid Approach in Label-free Immunosensing", Biosensors & Bioelectronics, vol. 8, 1993, pp. 387-392.

Brecht, A. et al., "Recent Developments in Optical Transducers for Chemical or Biochemical Applications," Sensors and Actuators B, Jan. 1997, pp. 1-7, vol. 38-39, Elsevier Science S.A., Lausanne, CH.

Brecht, A. et al., "Theoretical and Experimental Detectivity of the RIFS—transducer in Affinity-sensing", Biosensors 94, The Third World Congress on Biosensors: Abstracts, Oral Session, Jun. 2, 1994, p. 68.

Cao, L. et al., "Detection of Yersinia Pestis Fraction 1 Antigen With a Fiber Optic Biosensor", Journal of Clinical Microbiology, vol. 33, No. 2, Feb. 1994, pp. 336-341.

Christensen, D. et al., "Analysis of Excitation and Collection Geometries for Plannar Waveguide Immunosensors," SPIE vol. 1886, Fiber Optic Sensors in Medical Diagnostics, 1993, pp. 2-8.

Davies, R. et al., "An Optical Biosensor System for Molecular Interaction Studies", American Biotechnology Laboratory, Jul. 1993.

Elster, J. L. et al., "Optical Fiber Extrinsic Fabry-Perot Interferometric (EFPI)-Based Biosensors," Proceedings of the SPIE, 2000, pp. 105-112, vol. 3911.

Fabricius, N. et al., "A Gas Sensor Based on an Integrated Optical Mach-Zehnder Interferometer", Sensors and Actyators, vol. B7, 1992, pp. 672-676.

Gauglitz, G. et al., "Chemical and Biochemical Sensors Based on Interferometry at Thin (Multi-)Layers," Sensors and Actuators B, Mar. 1, 1993, pp. 21-27, vol. B11, No. 1-3.

Gauglitz, G. et al., "Interferometric Biochemical and Chemical Sensors," Proceeding of the SPIE, Jun. 1, 1995, pp. 41-48.

Gauglitz, G. et al., "Observation of Spectral Interferences for the Determination of Volume and Surface Effects of Thin Films", Analytical Biochemistry, vol. 341, 1991, pp. 279-283.

Hogg, D. et al., "Development of a Fiber Fabry-Perot Strain Gauge", SPIE vol. 1588, Fiber Optic Smart Structures and Skins IV, 1991, pp. 300-307.

Jorgenson, R. et al. "A Novel Surface Plasmon Resonance Based Fiber Optic Sensor Applied to Biochemical Sensing", SPIE, vol. 1886, 1993, pp. 35-48.

Kimoshita, Y. et al., "Sensing of Herbicide Residues Using Surface Plasmon Resonance Technique", The Third World Congress on Biosensors: Abstracts, 1994, p. 257.

Larvor, M.P. et al., "Measurement of the Dissociation Rate Constant of Antigen/Antibody Complexes in Solution by Enzyme-Linked Immunosorbent Assay," Journal of Immunological Methods, Apr. 15, 1994, pp. 167-175, vol. 170, No. 2.

Lim, S. et al., Application of an Interferometric Biosensor Chip to Biomonitoring an Endocrine Disruptor. Biotechnology and Bioprocess Engineering. 2004, vol. 9, No. 2, pp. 118-126.

Lin, C-J., et al., "A Novel in Vitro and in Situ Immunoassay Biosensor Based on Fiber Optic Fabry-Perot Interferometry," Proceedings of the SPIE, The International Society for Optical Engineering, 2004, pp. 304-307, vol. 5502, No. 1.

(56) References Cited

OTHER PUBLICATIONS

Lukosz, W., et al., "Output grating Coulers on Planar Optical Waveguides as Direct Immunosensors", Biosensors & Bioelectronics, vol. 6, 1991, pp. 227-232.

Lundstrom, I., et al. "Immunosensors Based on Surface Plasmon Resonance", The Third World Congress on Biosensors: Abstracts, 1991, p. 91.

Nikitin, P.I. et al., "New Direct Optical Biosensors for Multi-Analyte Detection," Sensors and Actuators B, Apr. 20, 2003, pp. 46-51, vol. 90, No. 1-3.

Ogert et al., "Detection of *Clostridium Botulinum* Toxin a Using a Fiber Optic-Based Biosensor", Analytical Biochemistry, vol. 205, 1992, pp. 306-312.
Philip et al., "Fiber Optic Immunochemical Sensor for Continuous, Reversible Measurement of Phenytoin," Clin. Chem., 1988, pp. 1417-1421, vol. 34/7.
Reagent Reservoirs with Control Wells, V&P Scientific, Inc., 2006, [online] [Retrieved on Sep. 6, 2006] Retrieved from the Internet <URL:http://www.vp-scientific.com/reagent.sub.--reservoirs.sub.--with.-sub.--control.sub.--.htm>.
Rich, R. L. et al., "A Global Benchmark Study Using Affinity-Based Biosensors," Analytical Biochemistry, Mar. 15, 2009, pp. 194-216, vol. 386, No. 2.
Rudraraju, S. et al., "Acoustic Wave Propagation in Composite Materials: an Experimental Study", SPIE, vol. 2191, Jul. 1994, pp. 487,493.
Schneider, I. et al., "Herbicide Detection Using Reaction, Centers Integrated Into Liposomes Binding to Grating Couplers", The Third World Congress on Biosensors: Abstracts, 1994, p. 271.
Tiefenthaler, K., "Grating Couplers as Label-free Biochemical Waveguide Sensors", Biosensors & Bioelectronics, vol. 8, No. 7-8, pp. xxxv-xxxvii.
Weber, A. et al., "Fiber-optic Fluorimetry in Biosensors: Comparison Between Evanescent Wave Generation and Distal-face Generation of Fluorescent Light", Biosensors & Bioelectronics, vol. 7, 1992, pp. 193-197.
Yang Y. et al., "Direct Monitoring of Antigen-Antibody Interactions by Optical Fiber Bioprobe," Proceedings of the SPIE, Jun. 8, 2003, pp. 431-436, vol. 5254, No. 1.
Yang, Y. et al., "Study of Optical Fiber Biosensor Based on White-Light Interferometry," Journal of Xi'An Jiaotong University, Sep. 2003, pp. 914-916, 988, vol. 37, No. 9, Xian, CN.
Yang Y. et al., "Direct Monitoring of Antigen-Antibody Interactions by Optical Fiber Bioprobe," Proceedings of the SPIE, Dec. 2003, pp. 431-436.
U.S. Appl. No. 12/240,823, filed Nov. 29, 2008, Zuk et al.

* cited by examiner

TIP TRAY ASSEMBLY FOR OPTICAL SENSORS

CROSS-REFERENCE TO RELATED APPLICATIONS

This application is a division of U.S. application Ser. No. 11/423,669, filed on Jun. 12, 2006 now abandoned, entitled "Tip Tray Assembly for Optical Sensors," which claims the benefit of U.S. Provisional Application No. 60/690,325, filed on Jun. 13, 2005, entitled "Tip Tray Assembly for Optical Sensors," both of which is hereby incorporated in their entirety, including any appendices or attachments thereof, in its entirety for all purposes.

BACKGROUND OF THE INVENTION

1. Field of the invention

The present invention relates to an apparatus and method based on fiber optic interferometry, and in particular, to a tip tray apparatus for packaging of optical sensors used in detecting analytes and mechanisms for creating flow of solution.

2. Description of the Related Art

Diagnostic tests based on a binding event between members of an analyte-anti-analyte binding pair are widely used in medical, veterinary, agricultural and research applications. Typically, such methods are employed to detect the presence or amount of an analyte in a sample, and/or the rate of binding of the analyte to the anti-analyte. Typical analyte-anti-analyte pairs include complementary strands of nucleic acids, antigen-antibody pairs, and receptor-receptor binding agent, where the analyte can be either member of the pair, and the anti-analyte molecule, the opposite member.

Diagnostics methods of this type often employ a solid surface having immobilized anti-analyte molecules to which sample analyte molecules will bind specifically and with high affinity at a defined detection zone. In this type of assay, known as a solid-phase assay, the solid surface is exposed to the sample under conditions that promote analyte binding to immobilized anti-analyte molecules. The binding event can be detected directly, e.g., by a change in the mass, reflectivity, thickness, color or other characteristic indicative of a binding event. Where the analyte is pre-labeled, e.g., with a chromophore, or fluorescent or radiolabel, the binding event is detectable by the presence and/or amount of detectable label at the detection zone. Alternatively, the analyte can be labeled after it is bound at the detection zone, e.g., with a secondary, fluorescent-labeled anti-analyte antibody.

Co-owned U.S. Pat. No. 5,804,453, (the '453 patent) which is incorporated herein by reference, discloses a fiber-optic interferometer assay device designed to detect analyte binding to a fiber-optic end surface. Analyte detection is based on a change in the thickness at the end surface of the optical fiber resulting from the binding of analyte molecules to the surface, with greater amount of analyte producing a greater thickness-related change in the interference signal. The change in interference signal is due to a phase shift between light reflected from the end of the fiber and from the binding layer carried on the fiber end, as illustrated particularly in FIGS. 7a and 7b of the '453 patent. The device is simple to operate and provides a rapid assay method for analyte detection.

The optical tip tray device described herein can be used with a fiber-optic inferometer assay device, as described above. Specifically it provides a mechanism for packaging and holding discrete fiber optic sensors in a format that allows for easy use of the sensors. Before the types of assays described above are conducted, the sensors can undergo some type of pre-wetting. Techniques can also be used to immobilize molecules, such as proteins, to the surface of the sensor. "Pre-wet," as used herein, is a procedure in which a sensor coated with immobilized binding proteins is hydrated to restore their biological activity. Sensors coated with proteins can be stored dry in order to preserve the activity of the proteins until they are to be used in an assay. In immobilization procedures, sensors are put into contact with sample solutions, such as protein-containing samples, and the proteins or other molecules in the sample are immobilized to the surface of biosensors coated with the appropriate surface chemistry. In the device disclosed herein, discrete optical sensors are packaged in a format (e.g., a format that corresponds to the 96-well format of a standard microtiter plate) that allows the sensors to be easily dipped into pre-wet or protein-immobilization solutions. Thus, in some embodiments, the device provides for off-line incubation, pre-wet, and/or immobilization. In contrast, current devices for holding biosensors are either in flow cell format or have sensors located as a part of the bottom of a microplate well, both of which require different pre-wetting and immobilization procedures. In addition, these systems do not provide flexibility for users to arrange or configure the biosensors to customize the sensor arrangement for immobilization. Users do not have the option to simply remove and save unused biosensors, but are instead forced to use an entire set of sensors for each experiment even if only a few were needed.

Therefore, there is a need for an easy mechanism for off-line incubation, pre-wetting, and immobilization where the user has the flexibility to move around the sensors and customize the arrangement. There is also a need for a device that stores these types of discrete sensors in a format for easy pick up of the sensors, for transfer of the sensors to a second microplate for assay, and for mapping of sensors to sample wells. Furthermore, these types of discrete sensors need to be packaged to avoid damage during shipping, handling, and storage of the sensors.

Current devices also have limitations with regard the mechanism for providing flow in wells during an assay. For molecular kinetic analyses and other types of analyses, the device must include some sort of mechanism for providing flow (e.g., within the wells of the microtiter plate containing sample or the second microtiter plate), for example, to measure the disassociation of molecules from the sensor surfaces. Where the sensor surface is located at the bottom of a microtiter plate, however, it is difficult to create any flow. Without proper flow, it is impossible to provide a valid environment for molecular binding kinetic analysis. Current systems use flow cells to create sample or buffer flow over the sensing surface. For example, some current systems use microfluidics and fluidic channels to move the fluid around to bring reagents into contact with a particular biosensor. However, these types of designs put a large design and support burden on the instrumentation. Thus, there is needed a mechanism that allows for fluidic motion without the need for microfluidics or fluidic channels. There is a need for a mechanism that allows exposure of the biosensor to a relatively large bulk of reagents by providing continuous flow of reagent over the biosensor.

The present invention is designed to overcome these and other limitations with a design that allows flexibility for arrangement or configuration of biosensors, biosensor mapping capability to sample wells in a microtiter plate, off-line incubation, pre-wet, and immobilization, and an effective mechanism for orbital flow of the reagent over the biosensors, among other advantages.

SUMMARY OF THE INVENTION

The invention includes, in one aspect, an apparatus and method for packaging of an optical sensing fiber. The apparatus includes a substrate with a plurality of openings, and each opening is configured for holding an optical sensing assembly. The assembly is positioned in the opening with a tip of the assembly extending through the opening to be suspended from the substrate. In addition, openings are arranged so the assembly positioned therein avoids contacting another assembly positioned therein. In some embodiments, the apparatus further includes a support member for supporting the substrate and positioning the substrate so the tip of the assembly suspended from the opening in the substrate contacts solution in one of a plurality of wells in a container adjacent to the substrate. The assembly can be configured for preparing of the optical assembly for assay.

In one particular design, the apparatus includes both a cover and a base that can lock together around the substrate to form an enclosure around the optical sensing assembly. A container (e.g., a microtiter plate) can be positioned inside the base, beneath the substrate, in a manner that allows the tips of the optical assemblies to line up in a predetermined orientation for immersion in the solution inside the wells of the container. The discrete optical assemblies can be moved around and arranged within the substrate to customize an array of assemblies. In some embodiments, the wells in the container are filled with different types of protein solution or another type of solution to customize the array. In some embodiments, different sensors (or sensors coated with different reagents) are arranged within the substrate to customize the array. The optical assemblies can be mapped to wells in a sample container or microtiter plate to allow a user to keep track of the samples being assayed and the different sensors being used in the assay.

In another aspect, the invention includes a method for packaging an optical sensing assembly for assay. The method includes placing a discrete optical sensing assembly in one of a plurality of openings in a substrate that is supported by a support member. The optical sensing assembly is positioned in the opening with a tip of the optical sensing assembly extending through the opening to be suspended from the opening in the substrate. In addition, the openings are arranged so the optical sensing assembly positioned therein avoids contacting another optical sensing assembly positioned therein. In some embodiments, the method further includes positioning the substrate so the tip of the optical sensing assembly suspended from the opening in the substrate contacts solution in one of a plurality of wells in a container adjacent to the substrate. In addition, the method can include preparing the optical sensing assembly for assay, such as by immobilization or pre-wet of the optical assembly before assay.

In one design, the substrate can hold the array of optical assemblies on a robotic instrument. In this embodiment, the substrate may or may not be positioned over a container of wells (e.g., a microtiter plate containing protein samples for immobilization on the sensor tips). One or more of the optical assemblies can be moved by a robotic arm from the tip tray apparatus to another location (e.g., a second microtiter plate containing samples and mounted on the robotic instrument next to the substrate). In some embodiments, the tip tray apparatus holds the sensors in position for manual transfer by a standard pipette or other device to another location (e.g., to a wastebasket or other location). Still other embodiments of the method include covering the substrate with a cover and setting the substrate over the container that is resting in a base. The base and cover can lock together to surround the optical sensing assembly for storage.

In yet another aspect, the invention includes an apparatus for maintaining flow of the solution. The apparatus includes an agitation assembly operably coupled to a container (e.g., the second sample-containing microtiter plate described above) with a plurality of wells containing solution. Each of the wells is configured for having a discrete optical sensing assembly immersed therein. The optical sensing assembly is also configured for measuring a characteristic of the solution. In addition, the agitation assembly comprises an agitation device that moves the container according to a specified type of motion to agitate the solution relative to the optical assembly to create flow of the solution relative to the optical assembly.

In one design, the agitation device can be a motor or an actuator, or other type of device for providing movement of the solution to create surface flow. The specified type of motion created by the agitation device can be a repetitive or a random motion of the solution, thus causing it to flow over the optical sensing assembly for the assay. In some embodiments, the apparatus is placed on a surface above the agitation device, and the device thereby causes movement or vibration of the solution relative to the optical sensing assembly.

In some embodiments of the invention, the substrate that holds an array of sensors (e.g., as part of the tip tray apparatus) over a first container (e.g., a first microtiter plate) is mounted on a robotic instrument adjacent to a sample container (e.g., a second microtiter plate containing sample) that is mounted on the agitation assembly within the robotic instrument. A robotic arm (e.g., a robotic system with 8 SMA's) can pick up one or more sensors (e.g., a row of eight sensors) and transfer them over to the second container outside the tip tray apparatus for dipping of the sensors in the sample contained in the second container.

These and other objects and features of the present invention will become more fully apparent when the following detailed description of the invention is read in conjunction with the accompanying drawings.

BRIEF DESCRIPTION OF THE SEVERAL VIEWS OF THE DRAWING

These and other features, aspects, and advantages of the present invention will become better understood with regard to the following description, and accompanying drawings, where.

DETAILED DESCRIPTION OF THE INVENTION

Definitions

Figure 1:
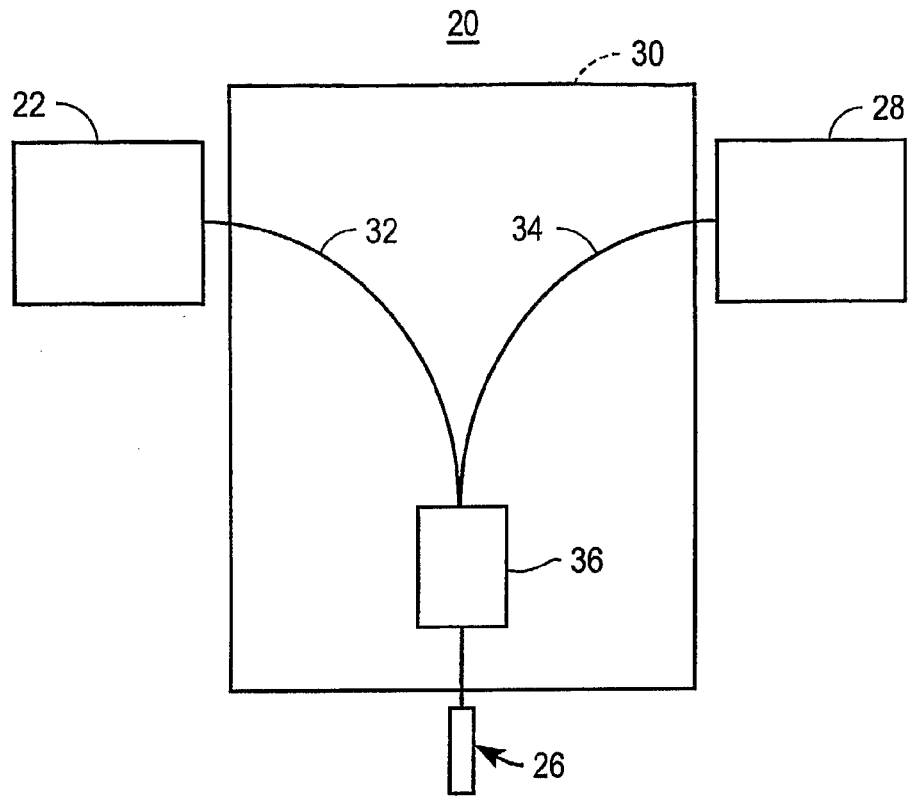
FIG. 1 shows the basic system setup for the biosensor and tip tray apparatus, according to an embodiment of the invention.

Terms used in the claims and specification are to be construed in accordance with their usual meaning as understood by one skilled in the art except and as defined as set forth below. Numeric ranges recited in the claims and specification are to be construed as including the limits bounding the recited ranges.

The term "in vivo" refers to processes that occur in a living organism.

An "analyte-binding" molecule refers to any molecule capable of participating in a specific binding reaction with an analyte molecule. Examples include but are not limited to, e.g., antibody-antigen binding reactions, and nucleic acid hybridization reactions.

A "specific binding reaction" refers to a binding reaction that is saturable, usually reversible, and that can be competed with an excess of one of the reactants. Specific binding reactions are characterized by complementarity of shape, charge, and other binding determinants as between the participants in the specific binding reaction.

An "antibody" refers to an immunoglobulin molecule having two heavy chains and two light chains prepared by any method known in the art or later developed and includes polyclonal antibodies such as those produced by inoculating a mammal such as a goat, mouse, rabbit, etc. with an immunogen, as well as monoclonal antibodies produced using the well-known Kohler Milstein hybridoma fusion technique. The term includes antibodies produced using genetic engineering methods such as those employing, e.g., SCID mice reconstituted with human immunoglobulin genes, as well as antibodies that have been humanized using art-known resurfacing techniques.

An "antibody fragment" refers to a fragment of an antibody molecule produced by chemical cleavage or genetic engineering techniques, as well as to single chain variable fragments (SCFvs) such as those produced using combinatorial genetic libraries and phage display technologies. Antibody fragments used in accordance with the present invention usually retain the ability to bind their cognate antigen and so include variable sequences and antigen combining sites.

A "small molecule" refers to an organic compound having a molecular weight less than about 500 daltons. Small molecules are useful starting materials for screening to identify drug lead compounds that then can be optimized through traditional medicinal chemistry, structure activity relationship studies to create new drugs. Small molecule drug compounds have the benefit of usually being orally bioavailable. Examples of small molecules include compounds listed in the following databases: MDL/ACD (http://www.mdli.com/), MDL/MDDR (http://www.mdli.com/), SPECS (http://www.specs.net/), the China Natural Product Database (CNPD) (http://www.neotrident.com/), and the compound sample database of the National Center for Drug Screening (http://www.screen.org.cn/).

Abbreviations used in this application include the following: "ss" refers to single-stranded; "SNP" refers to single nucleotide polymorphism; "PBS" refers to phosphate buffered saline (0.01 M phosphate buffer, 0.0027 M potassium chloride and 0.137 M sodium chloride, pH 7.4); "NHS" refers to N-hydroxysuccinimide; "MW" refers to molecular weight; "Sulfo-SMCC" refers to sulfosuccinimidyl 4[N-maleimidomethyl]cyclohexane-1-carboxylate.

It must be noted that, as used in the specification and the appended claims, the singular forms "a," "an" and "the" include plural referents unless the context clearly dictates otherwise.

Advantages and Utility

The advantages and utility of the invention are illustrated by reference to the Figures and Examples as described in greater detail below. These include an apparatus that holds and stores discrete optical fiber sensors in a format that is useful for off-line pre-wetting or protein immobilization, for transfer with a robotic or other type of instrument, etc. In some embodiments, a substrate holds the sensors in a format that corresponds to a standard 96-well microplate (i.e., an 8×12 format with approximately 9 mm spacing between the sensors). This positioning allows a microplate or other container to be placed in the tip tray apparatus under the sensors so that each tip of each sensor is suspended over and can be immersed in a liquid in the microplate wells. This design provides a means for immersing the end of the sensor so that the tips of the sensors do not have to rub against or otherwise contact the sides of the package or one another, thus protecting them from contamination or damage.

Holding the sensors in this type of format can serve a number of purposes. As one example, this format can be useful in pre-wetting of the sensors. The sensors can be coated with immobilized binding proteins and stored dry in order to preserve the activity of the proteins. Then a container, such as a microtiter plate, containing simple buffer or other solution can be placed in the tip tray beneath the sensors to immerse the tips of the sensors in the buffer. This immersion allows the sensors to become hydrated, thus restoring their biological activity prior to their transfer to the sample containing microplate (e.g., a second microtiter plate outside the tip tray) for assay. As another example, this format can be useful in immobilization of molecules, such as proteins, to the surface of the sensors (or e.g., for measurement of interaction with another protein already immobilized on the optical sensing assembly). For example, protein-containing samples can be dispensed into microplate wells and the microplate can be placed in the tip tray under the tips of the sensors that have the appropriate surface chemistry so that binding of the protein to the sensor occurs. These samples may be, e.g., the same for all wells or different in different wells for preparing a homogenous or heterogenous set of sensors. Since protein immobilization does not entail optical thickness measurements, the immobilization procedure can be performed off-line or outside of the use of the instrument for assay (i.e., in some embodiments the sensors do not have to be on the robotic instrument during immobilization).

Another advantage of the apparatus described herein is that the biosensors are each discrete structures that do not have to be connected to one another or connected to the apparatus that supports them (e.g., they are not located at the bottom of microplate wells, etc), so a user can move around the various sensors or customize the arrangement as desired. Since the sensors are discrete, the user can remove and save extra sensors that are not needed for a smaller-sized assay, rather than wasting these unused sensors as might occur in an apparatus where the sensors are located at the bottom of microplate wells. In addition, as described above, the tip tray apparatus can have a microtiter plate or other container optionally placed inside the base of the tip tray apparatus for pre-wet (pre-conditioning of tips) or off-line immobilization of proteins, and different proteins can be used in each well of the plate, thereby allowing for a customized array of sensor tips.

A further advantage includes the ability to map the sensors and their specific arrangement to the sample container (e.g., a second microtiter plate outside of the tip tray) including wells filled with sample. The position of each sensor can be mapped to the corresponding position of the well of sample that the sensor will contact during assay. Yet other advantages include the design of the sensors that allow them to be positioned for automatic pick-up and usage by a robotic instrument or by a standard pipette. In embodiments in which the sensors are positioned in a 96-well format, the sensors can then be easily transferred to a second microplate for measurement. Furthermore, the overall apparatus is configured to protect the sensors during shipping, handling, and storage. The sensors rest neatly in separate openings in the apparatus and, in some embodiments, the apparatus includes a hard-sided bottom portion and a top portion that effectively surround the sensors in a safe and protected environment.

A further advantage is provided in the mechanism for creating orbital flow without the need for microfluidics and fluidic channels. As described above, this is needed for providing a valid environment for molecular binding kinetic analysis. In the invention described herein, an orbital agitation device is provided for creating relative motion between an optical fiber sensor surface and the samples in a microtiter plate. In one embodiment, the plate is rotated in a plane that is perpendicular to the fiber sensors. An angle between the plate bottom and sensor fibers is also possible to reduce the reflected light (i.e., background noise).

FIG. 1 shows, in schematic view, an interferometer system 20 constructed in accordance with the invention. In its most basic elements, the system 20 includes a light source 22, a biosensor or optical sensing assembly 26 that functions as a sensing element or detector tip, and a detector unit 28 for detecting interference signals produced by interfering light waves reflected from the optical sensing assembly 26.

Light from source 22 is directed onto the optical sensing assembly 26, and reflected back to the detector through an optical coupling assembly indicated by dashed lines at 30. In a preferred embodiment, the coupling assembly includes a first fiber cable 32 extending from the light source 22 to the optical sensing assembly 26, and a second fiber cable 34 which carries reflected light from the optical sensing assembly 26 to the detector 28. Optionally, an optical coupler may be used to optically couple the fiber cables 32, 34 to the optical sensing assembly 26.

The light source 22 in the system 20 can be a white light source, such as a light emitting diode (LED) which produces light over a broad spectrum, e.g., 400 nm or less to 700 nm or greater, typically over a spectral range of at least 100 nm. Alternatively, the light source 22 can be a plurality of sources each having a different characteristic wavelength, such as LEDs designed for light emission at different selected wavelengths in the visible light range. The same function can be achieved by a single light source 22, e.g., white light source, with suitable filters for directing light with different selected wavelengths onto the optical sensing assembly 26.

The detector 28 can be a spectrometer, such as charge-coupled device (CCD), capable of recording the spectrum of the reflected interfering light from the optical sensing assembly 26. Alternatively, where the light source 22 operates to direct different selected wavelengths onto the optical sensing assembly 26, the detector 28 can be a simple photodetector for recording light intensity at each of the different irradiating wavelengths. In still another embodiment, the detector 28 can include a plurality of filters which allows detection of light intensity, e.g., from a white-light source, at each of a plurality of selected wavelengths of the interference reflectance wave.

Figure 2:
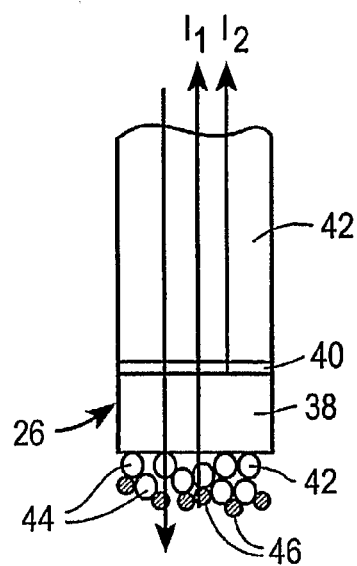
FIG. 2 shows an interferometer system constructed according to an embodiment of the invention.

FIG. 2 shows the optically functional part of an optical sensing assembly 26 constructed in accordance with one embodiment of the invention. The optical sensing assembly 26 includes a short length of optical fiber 42, to which the remainder of the optical sensing assembly 26 is fixedly attached. The other end of optical fiber 42 couples to the fiber cables 32 and 34, respectively. As seen, the assembly 26 includes a transparent optical element 38 having first and second reflecting surfaces 42, 40 formed on its lower (distal) and upper (proximal) end faces, respectively. According to an important feature of the invention, the thickness "d" of the optical element 38 between its distal and proximal surfaces, i.e., between the two reflecting surfaces, is at least 50 nm, and preferably at least 100 nm. An exemplary thickness is between about 100-5,000 nm, preferably 400-1,000 nm. The first reflecting surface 42 is formed of a layer of analyte-binding molecules, such as molecules 44, which are effective to bind analyte molecules 46 specifically and with high affinity. That is, the analyte and anti-analyte molecules are opposite members of a binding pair of the type described above, which can include, without limitations, antigen-antibody pairs, complementary nucleic acids, and receptor-binding agent pairs.

The index of refraction of the optical element 38 is preferably similar to that of the first reflecting surface 42, so that reflection from the lower distal end of the end optical sensing assembly 26 occurs predominantly from the layer formed by the analyte-binding molecules 44, rather than from the interface between the optical element 38 and the analyte-binding molecules 44. Similarly, as analyte molecules 46 bind to the lower layer of the optical sensing assembly 26, light reflection form the lower end of the assembly 26 occurs predominantly from the layer formed by the analyte-binding molecules 44 and bound analyte 46, rather than from the interface region. One exemplary material forming the optical element 38 is $SiO_2$, e.g., a high-quality quality glass having an index of refraction of about 1.4-1.5. The optical element 38 can also be formed of a transparent polymer, such as polystyrene or polyethylene, having an index of refraction preferably in the 1.3-1.8 range.

The second reflecting surface 40 in the optical sensing assembly 26 formed as a layer of transparent material having an index of refraction that is substantially higher than that of the optical element 38, such that this layer functions to reflect a portion of the light directed onto the optical sensing assembly 26. Preferably, the second layer has a refractive index greater than 1.8. One exemplary material for the second layer is $Ta_2O_5$ with refractive index equal to 2.1. The layer is typically formed on the optical element 38 by a conventional vapor deposition coating or layering process, to a layer thickness of less than 50 nm, typically between 5 and 30 nm.

The thickness of the first (analyte-binding) layer is designed to optimize the overall sensitivity based on specific hardware and optical components. Conventional immobilization chemistries are used in chemically, e.g., covalently, attaching a layer of analyte-binding molecules to the lower surface of the optical element. For example, a variety of bifunctional reagents containing a siloxane group for chemical attachment to $SiO_2$, and an hydroxyl, amine, carboxyl or other reaction group for attachment of biological molecules, such as proteins (e.g., antigens, antibodies), or nucleic acids. It is also well known to etch or otherwise treat glass a glass surface to increase the density of hydroxyl groups by which analyte-binding molecules can be bound. Where the optical element 38 is formed of a polymer, such as polystyrene, a variety of methods are available for exposing available chemically-active surface groups, such as amine, hydroxyl, and carboxyl groups.

The analyte-binding layer 44 is preferably formed under conditions in which the distal surface of the optical element 38 is densely coated, so that binding of analyte molecules 46 to the layer forces a change in the thickness of the layer, rather than filling in the layer. The analyte-binding layer 44 can be either a monolayer or a multi-layer matrix.

The measurement of the presence, concentration, and/or binding rate of analyte 46 to the optical sensing assembly 26 is enabled by the interference of reflected light beams from the two reflecting surfaces 40, 42 in the optical sensing assembly 26. Specifically, as analyte molecules 46 attach to or detach from the surface, the average thickness of the first reflecting layer 42 changes accordingly. Because the thickness of all other layers remains the same, the interference wave formed by the light waves reflected from the two surfaces is phase shifted in accordance with this thickness change.

Assume that there are two reflected beams: The first beam is reflected from the first surface, which is the distal end interface between analyte-binding molecules 44 and bound analyte 46 and the surrounding medium; and the second beam is reflected from the second surface, which is the proximal interface between the optical element (the first layer) and the high-index of refraction layer (the second layer). The overall wavelength-dependent intensity of the interference wave is:

$$I = I_1 + I_2 + 2\sqrt{I_1 I_2} \cos\left(\frac{2\pi\Delta}{\lambda}\right)$$

where I is the intensity, $I_1$ and $I_2$ are the intensity of two interference beams, $\Delta$ is the optical path difference, and $\lambda$ is the wavelength.

When $(2\pi\Delta/\lambda)=N\pi$, the curve is at its peak or valley if N is an integer 0, 1, 2, .... The thickness of the first layer $d=\Delta/2n$. Therefore, $\lambda=4$ nd/N at peaks or valleys (extrema). For the first several values of N, i.e., 0, 1, 2, . . . 7, and assuming a d of 770 nm, the equation gives:

$N=0: \lambda=\infty$ (peak)

$N=1: \lambda=4nd=4,496.80$ nm (Valley)

$N=2: \lambda=2nd=2,248.40$ nm (Peak)

$N=3: \lambda=4nd/3=1,498.9$ nm (Valley)

$N=4: \lambda=nd=1,124.20$ nm (Peak)

$N=5: \lambda=4nd/5=899.36$ nm (Valley)

$N=6: \lambda=2nd/3=749.47$ nm (Peak)

$N=7: \lambda=4nd/7=642$ nm (Valley)

$N=8: \lambda=nd/2=562$ nm (Peak)

$N=9: \lambda=4nd/9=499.64$ nm (Valley)

$N=10: \lambda=4nd/10=449.6$ nm (Peak)

Figure 3A:
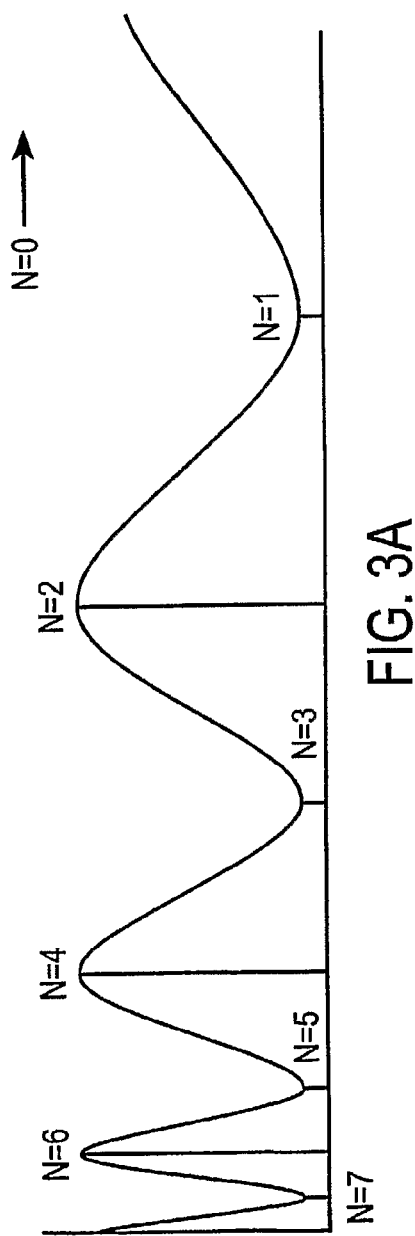
FIGS. 3A and 3B show a portion of an interference wave over 7 peak and valley orders (3A), and over in a visible portion of the spectrum (3B)
Figure 3B:
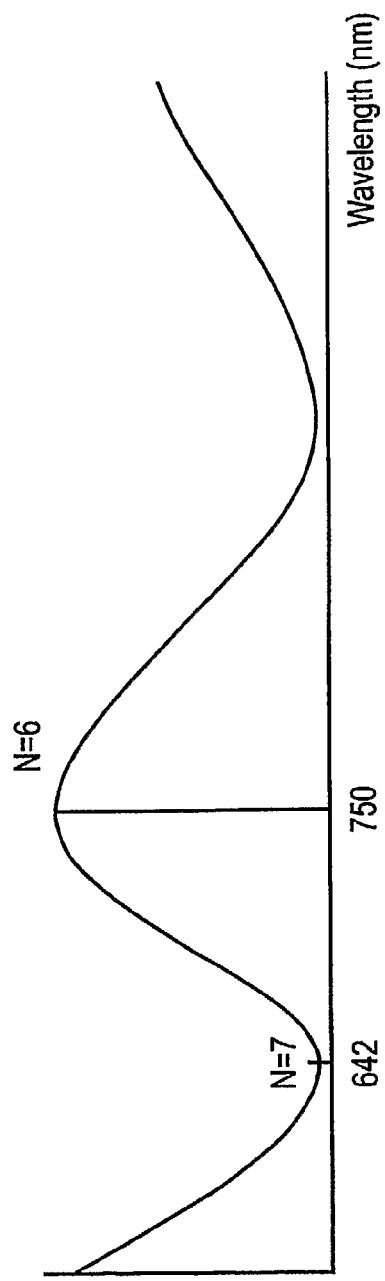

As can be seen, and illustrated further in FIGS. 3A and 3B, at least three peaks/valleys (N=7-9) occur in the visible spectral range.

If the $7^{th}$ order valley is used to calculate the change in molecular layer thickness, when the molecular layer attached to the first layer increases from 0 nm to 10 nm, the $7^{th}$ order valley will shift to 650.74 nm. Therefore, the ratio between the actual the phase shift of the $7^{th}$ order valley and thickness change equals (650.74−642.40)/10=0.834.

By contrast, if the initial spacing between the two reflecting layers 40, 42 is made up entirely of the analyte-binding molecules 44 on the end of the fiber, assuming a thickness of this layer of 25 nm, then the first order peak will occur at 146 nm, clearly out of the range of the visible spectrum, so that the device will only see a portion of the region between the 0-order valley and the first order peak, but will not see any peaks, making a shift in the spectral characteristics of the interference wave difficult to measure accurately.

Not until the total thickness of the reflecting layer approaches about 100 nm will the first-order peak appear in the visible spectrum. Assuming a total thickness change of up to 50 nm, the thickness of the optical element can then be as small as 50 nm, but is preferably on the order of several hundred nm, so that the phase shift or change in periodicity of the interference wave can be measured readily by a shift in the spectral positions of higher-order peaks or valleys, e.g., where N=3-10.

The ratio between the actual thickness and the measured phase shift is considered as a key factor of measurement sensitivity. It can be appreciated how one can adjust the thickness of the optical element 38 and its refractive index to improve and optimize the sensitivity to accommodate the electronics and optical designs.

Figure 4:
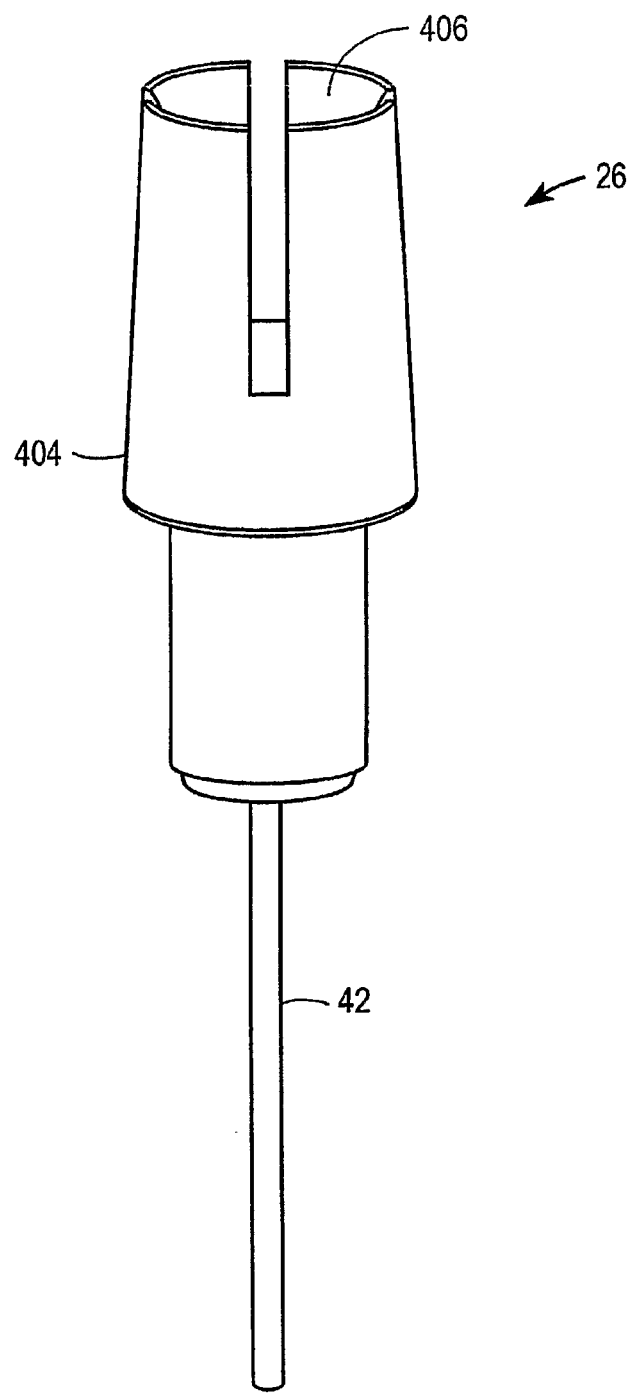
FIG. 4 shows an optical sensing assembly constructed according to an embodiment of the invention.

Referring now to FIG. 4, there is shown an illustration of a side view of the full optical sensing assembly 26 (or biosensor or sensor), according to an embodiment of the invention. The sensors can be fabricated from cut lengths of optical fiber 42 bonded into a hub 404, similar in structure to a hypodermic needle and its hub. A portion of the fiber 42 can be immersed in sample during an assay. As shown in FIG. 2, a portion of the fiber 42 can be coated with a substance, such as analyte-binding molecules 44, to which the sample (e.g., analyte molecules 46) will bind. In some embodiments, the analyte-binding molecule is a protein, a small molecule, a nucleic acid, a carbohydrate, or some other type of molecule. Where the molecule is a protein, the protein can be an avidin, a streptavidin, an antibody, an antibody fragment, or another type of protein. In some embodiments, the optical sensing assembly 26 is used to measure the amount of analyte in the sample based on the amount of analyte that binds to the analyte-binding molecule coated on the assembly 26. In other embodiments, the optical sensing assembly 26 is used to measure the kinetics of a binding reaction between the analyte in the sample and the analyte-binding molecule coated on the optical sensing assembly.

Before these types of assays are conducted, the optical sensing assemblies 26 can be immersed in a specific molecule-containing immobilization solution for immobilization of molecules, such as proteins, to the assemblies 26 that are coated with the appropriate surface chemistry for this immobilization. Similarly, the assemblies 26 can be immersed into a pre-wet solution to hydrate the sensors restoring biological activity of previously bound molecules (e.g., binding proteins) just prior to the transfer of the sensors to a second microplate or other container for assay, as explained above.

The hub 404 of the optical sensing assembly 26 extends from fiber 402 and provides a base onto which a robotic instrument, standard pipette, or other instrument can attach to the sensor and move it from a first location to a second location. Specifically, the instrument used for moving the optical sensing assembly 26 can be attached at opening 406, and the assembly 26 can thus be moved to a different location as desired. The instrument for moving the assembly 26 can be designed for moving an array of assemblies 26 at one time, and thus the instrument can pick up a number of the discrete assemblies 26 from the tip tray holding the assemblies 26 (see FIG. 5) to move the assemblies 26 to a second location (e.g., a second microtiter containing sample to be tested).

Figure 5:
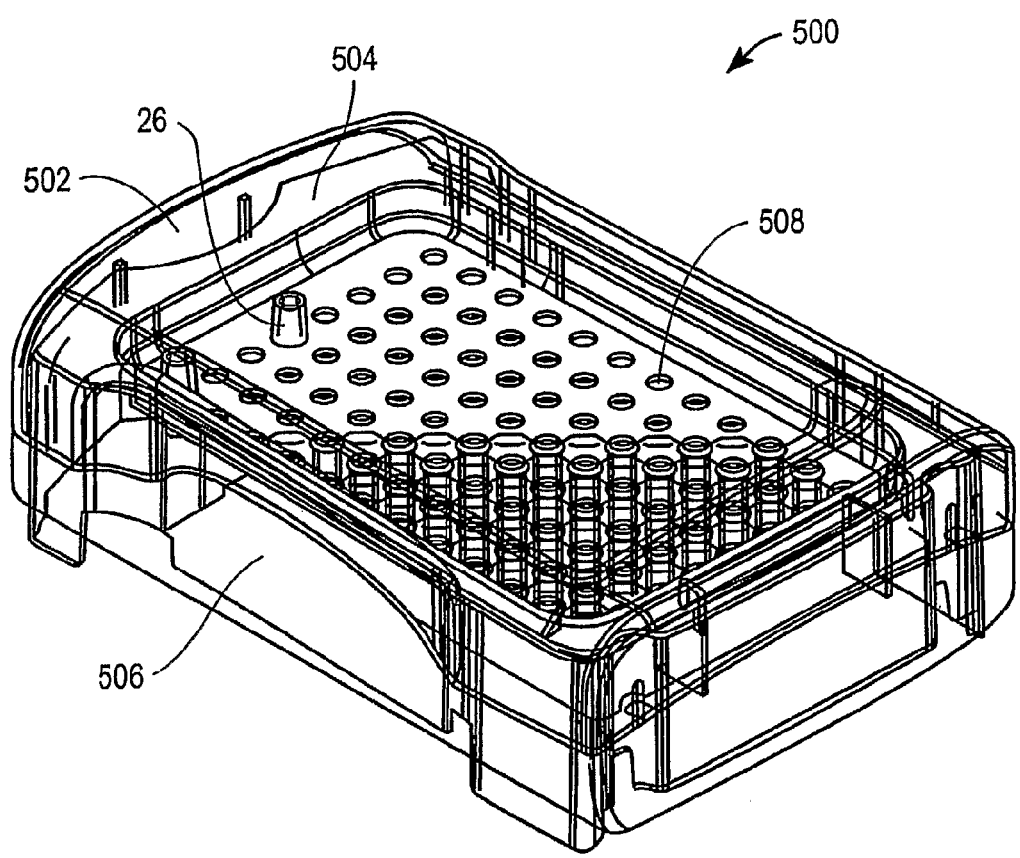
FIG. 5 shows an apparatus including a substrate and an optical sensing assembly stored in an opening in the substrate, according to an embodiment of the invention.

FIG. 5 shows a tip tray apparatus 500 for packaging one or more optical assemblies 26, according to an embodiment of the present invention. The tip tray apparatus 500 includes a substrate 504, which is the portion of the tip tray apparatus 500 that includes a number of openings 508 for containing one or more discrete optical assemblies 26. The optical sensing assemblies 26 are discrete in that they are not connected or attached directly to other optical assemblies 26, and each assembly 26 can be moved around within the tip tray 500 to any configuration the user selects. Other devices may be attached to the optical sensing assemblies 26 in the tray 500, such as a standard pipette device, a robotic instrument, an optical fiber assembly (as shown in FIG. 1), etc., and these devices may indirectly and temporarily link these assemblies 26 together for a particular purpose. However, the user can still have the ability to move the assemblies 26 around at some point to configure them for the assay. In some embodiments, the optical sensing assemblies 26 are disposable tips that are to be used for an assay and then thrown away and replaced by new tips for the next assay.

The optical assemblies 26 are suspended in the openings 508 with the tip of the optical sensing assembly 26 extending away from the substrate 504. Each discrete optical sensing assembly 26 can rest in an opening 508 in the substrate 504, and the optical sensing assembly 26 is positioned in the opening so that the tip of the optical sensing assembly 26 is suspended below the substrate 504 while the hub of the optical sensing assembly 26 rests above the substrate 504. Thus, in FIG. 5, the hub 404 portion of the optical sensing assembly 26 can be seen resting above the opening 508, while the fiber 42 portion of the assembly 26 is positioned through the opening 508 and below the substrate 504. In some embodiments, the optical sensing assembly 26 rests loosely within the opening 508. In other embodiments, the optical sensing assembly 26 is snapped or locked into place in the opening 508. In some embodiments, the substrate 504 includes an array of 96 openings 508 in an 8×12 pattern, similar to the structure of the wells in a standard 96-well microtiter plate. In other embodiments, the substrate 504 includes an array of 384 openings 508 or 1536 openings, similar to the wells in a standard 384-well or 1536-well microtiter plate. However, the array of openings 508 can be arranged in a number of other ways and can include any other number of openings 508, as suitable. In general, the openings are arranged so that the optical sensing assemblies 26 positioned in the openings avoid contacting other optical sensing assemblies 26, and thus the optical sensing assemblies 26 remain as discrete sensors within the tip tray.

Also illustrated in FIG. 5 is a base structure 506 and a cover 502 that make up a part of tip tray apparatus 500. The substrate 504 rests on the base 506 and the cover 502 rests on top of the base 506 to enclose the upper portion of the substrate 504. In this manner, the optical assemblies 26 in the substrate 504 are protected from the environment in the closed compartment created by base 506 and cover 502. The optical assemblies 26 can be stored in an enclosed manner for protection, and the assemblies 206 can also be protected during shipping and handling. The hard-sided base 506 and cover 502 can lock into an enclosed position and thus protect the contents of apparatus 500. The base 506 and cover 502 can form an injection-molded plastic box, as shown in FIG. 5, or the apparatus 500 can be constructed from materials other than plastic. As shown in FIG. 5, the cover 502 can be transparent or translucent, allowing the user to see the optical assemblies 26 and substrate 504 beneath the cover 502.

Figure 6:
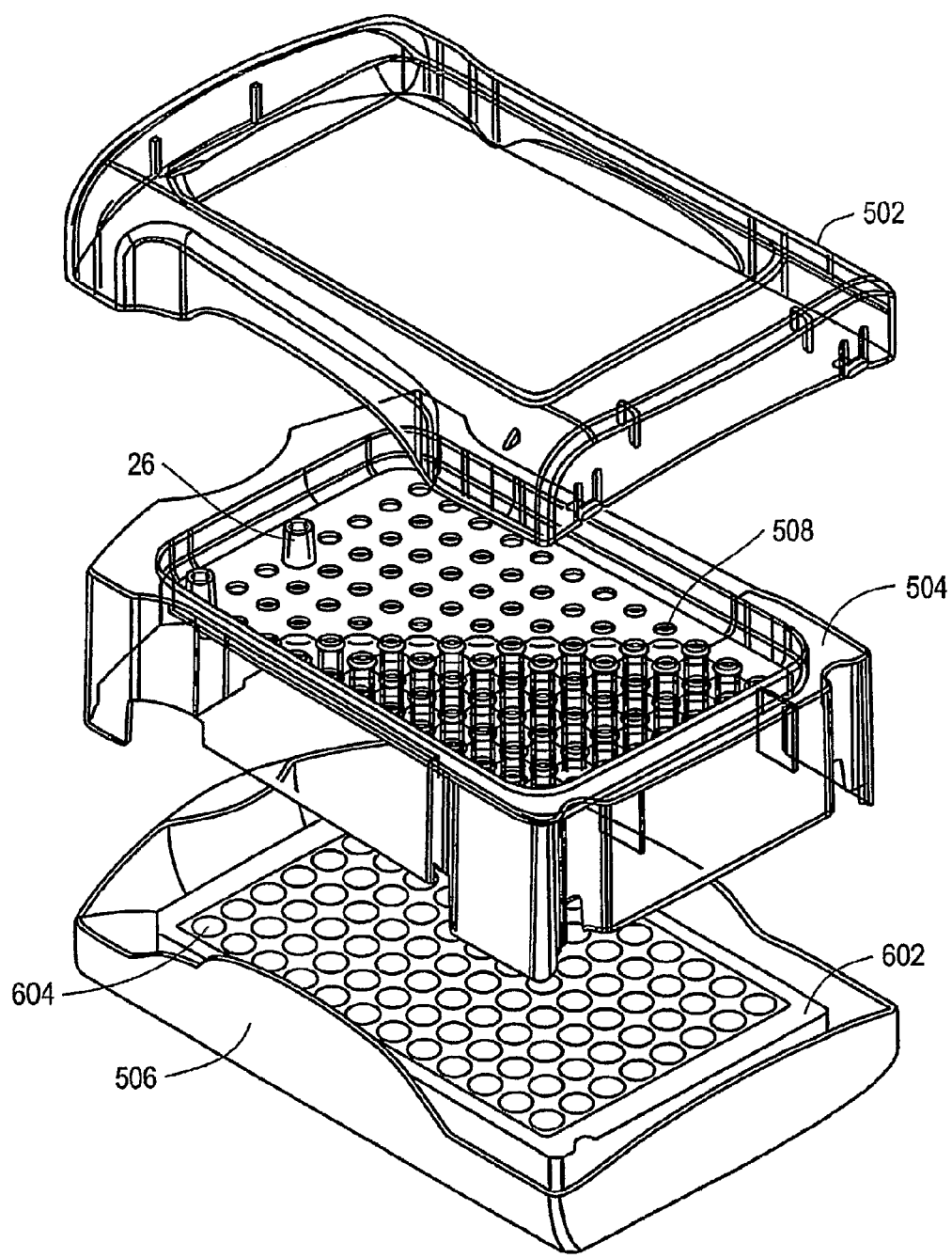
FIG. 6 shows an exploded view of the apparatus illustrating a cover, a substrate, a base, and a container of wells, according to an embodiment of the invention.

Referring now to FIG. 6, there is shown an exploded view of the tip tray apparatus 500, according to an embodiment of the invention. This Figure illustrates how the various pieces of the tip tray apparatus 500 fit together. As shown in FIG. 5, each of the pieces of the apparatus can be completely separated from one another. The cover 502 can be completely removed from the substrate 504 and base 506, to expose the optical assemblies 26 below. Furthermore, the substrate 504 can be completely separated from the base 506 to expose container 602 below. Container 602 can be a standard 96-well, 384-well, or 1536-well microtiter plate that includes an array of wells 604 for holding sample. Container 602 can also include any other number of wells (e.g., 1 well, 8 wells, 384 wells, etc.) and any other well arrangement or overall configuration, as desired. Container 602 can be an injection-molded plastic plate, as shown in FIG. 5, or container 602 can be made of another material, as suitable.

As FIG. 6 illustrates, the openings 508 in the substrate 504 correspond generally with the wells 604 in container 602. When the tip of an optical sensing assembly 26 is placed into an opening 508 in the substrate 504, the fiber 42 portion (not shown) of the optical sensing assembly 26 will extend below the substrate 504 and into the well 604 of container 602. The substrate 504 can be arranged to be a distance from container 602 that permits a portion of fiber 42 (not shown) of the optical sensing assembly 26 to be immersed in sample contained in the well 604. The container 602 can also be separated from the base 506 to allow the container to be removed from the apparatus 500. Thus, a user can place pre-wet or immobilization solution in the wells 604, for example, while the container 602 is separate from the tip tray apparatus 500, and the user can then insert the container 602 into the base 506 when the wells 604 have been filled. In addition, the substrate 504 can be used by itself without the container 602. For example, the substrate 504 can be mounted on a robotic instrument and can simply hold the optical assemblies in place for a robotic arm to attach to one or more of the assemblies and move the assemblies to a container of sample to be tested (e.g., a microtiter plate that is separate from the tip tray apparatus). In this example, the container 602 can be included under the substrate 504 on the robotic instrument, but the container 602 can be optionally left out, as desired.

The apparatus 500 described herein is useful in a number of ways. As described previously, the apparatus 500 is useful in orienting and positioning the optical assemblies 26 (i.e., in a 96-well format) so that they can easily be picked up by a robotic instrument or a standard pipette and transferred to another location. In addition, the apparatus 500 protects the optical sensing assemblies 26 during shipping, handling, and storage by enclosing them within a protected compartment. The apparatus 500 also provides a means to map selected sensors to selected wells in a microtiter plate or other container. Furthermore, as explained above, the apparatus can be used in incubation, immobilization, pre-wet, etc. In some embodiments, the immobilization is conducted off-line, separate from the robotic instrument used for assay. However, in some embodiments, the substrate 504 plus container 602 filled with solution for immobilization of molecules to the optical assemblies 26 (e.g., protein solution) can be placed onto the robotic instrument. In some embodiments, the immobilization step occurs while the substrate 504 is on the instrument.

In some embodiments, the apparatus 500 or some of the components of the apparatus 500 can be mounted on a robotic system, as described above. In some embodiments, the substrate 504 is placed above a first microtiter plate containing samples or solution (e.g., protein immobilization solution). The substrate 504 can be mounted alongside a second microtiter plate (that is separate from the substrate 504) also mounted on the robotic system. The second plate can contain the same or different samples included in the first plate. One or more of the optical assemblies 26 in the substrate 504 can be picked up with a robotic system and transferred to the second plate for immersion in the samples to be tested. In some embodiments, the first microtiter plate is not included, and instead only the substrate 504 is mounted on the instrument. In some embodiments, the second plate is mounted on an agitation assembly for creating orbital flow of sample within the wells of the second plate, as will be described in more detail below. In still other embodiments, the substrate 504 (or possibly a second substrate 504) is used to position the sensors over the second microtiter plate (or over another container holding samples to be tested) during an assay.

Numerous different types of assays can be conducted using the discrete optical assemblies 26. For example, assays can involve an anti-species antibody carried on the sensor tip, for screening hybridoma expression lines for cell lines with high antibody expression, or an antigen carried on the tip, to characterize high affinity antibodies against that antigen. Other assays can include a protein carried on the tip, for identifying and characterizing binding partners (DNA, RNA, proteins, carbohydrates, organic molecules) for that protein, or a carbohydrate or glycosyl moiety carried on the tip, for identifying and characterizing binding partners (such as, e.g., DNA, RNA, proteins, carbohydrates, organic molecules) for that carbohydrate. Still other assays can include a protein thought to participate in a multi-protein complex carried on the tip, for characterizing the binding components and/or kinetics of complex formation, or a small protein-binding molecule carried on the tip, for identifying and characterizing protein binders for that molecule. These are but a few examples of assays that could be conducted, and these are in no way meant to limit the scope of the invention.

In some embodiments, every opening 508 in the substrate 504 contains an optical sensing assembly 26, and every well 604 in container 602 contains a solution (i.e., an immobilization or pre-wet solution, a sample, etc.) that is contacted by each optical sensing assembly 26. However, the user can move around the assemblies 26 and customize the array of assemblies 26, as desired. For example, the user may wish to only use one row of optical assemblies 26 for an assay, and may use only a corresponding row of wells 604 in container 602. The user can leave all of the other openings 508 in the substrate 504 and all of the other wells 604 in the container 602 empty during pre-wetting and immobilization, for example. In this manner, the user can avoid wasting a number of sensors needlessly by simply omitting the sensors that are not going to be used during an assay. In contrast, in an apparatus in which the sensors are all included at the bottom of wells in a microtiter plate, an entire set of sensors must be used for each assay, even if the assay only includes 10 wells filled with sample. In some embodiments, the user may wish to use different types of samples or protein immobilization solutions in different wells 604 or different kinds of optical assemblies 26 (or assemblies 26 with different coatings on the tip) to customize the array.

As explained above, the apparatus 500 arranges the optical assemblies 26 in a manner that allows the optical assemblies 26 to be mapped to the array of wells in the sample container or second microtiter plate that will be used in conducting the assay. A combination of software can provide programmable control of the sample plate and of which samples are tested and/or which sensors are used (e.g., different sensors coated with different proteins). In some embodiments, the user can view the assay on a computer display or other type of display, and thus can see which wells in the sample plate are filled with which types of sample and/or can keep track of which sensors are used and into which sample wells these sensors are dipped into in the sample-containing second microtiter plate. In this manner, the user will know what optical assemblies 26 are associated with what samples.

Figure 7:
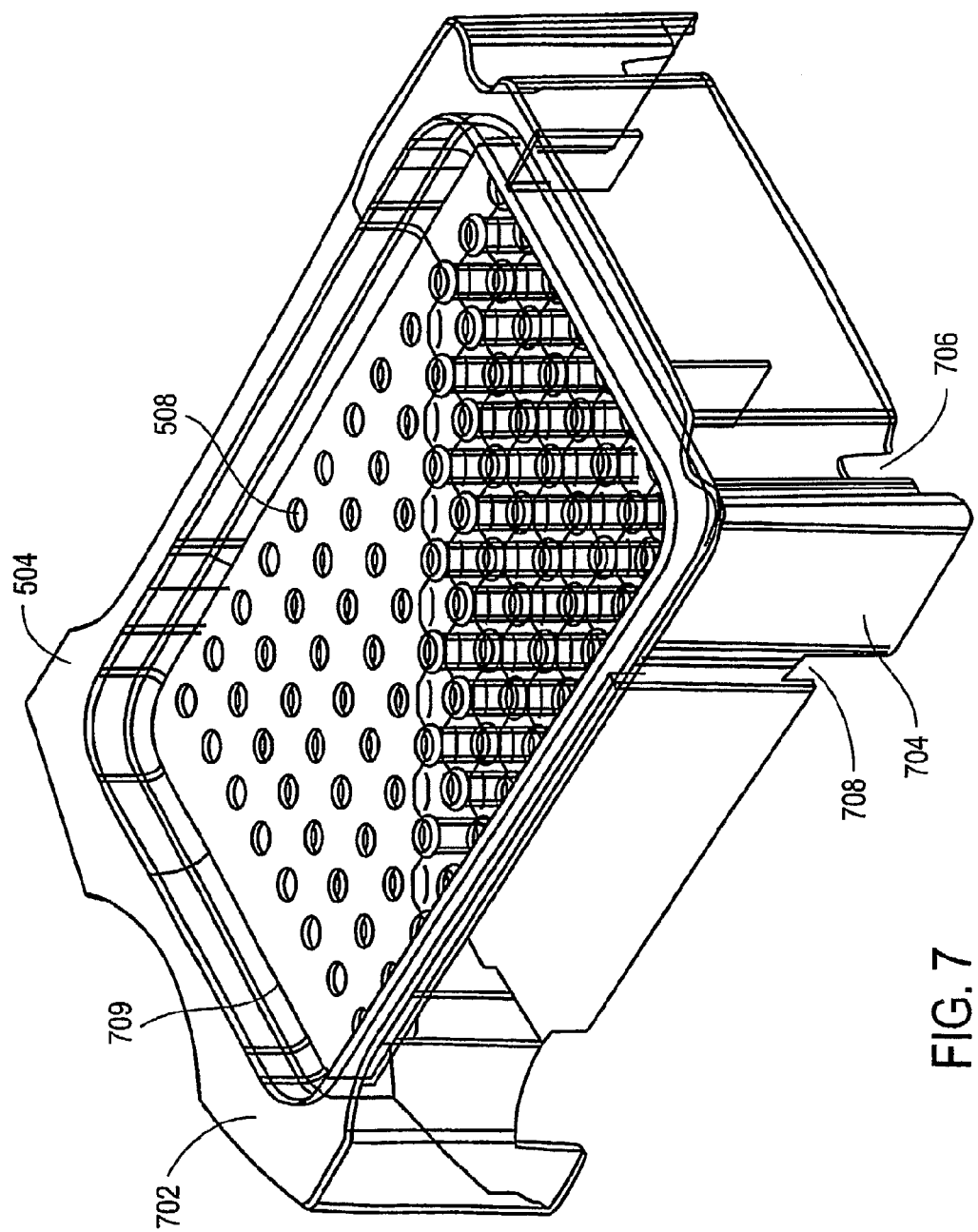
FIG. 7 shows perspective view of the substrate with an array of openings therein, according to an embodiment of the invention.

Referring now to FIG. 7, there is shown an illustration of the substrate 504 and openings 508, according to an embodiment of the invention. The openings 508 of the substrate 504 extend down below the substrate 504 to a sufficient distance to prevent the optical assemblies 26 inside the openings 508 from tilting or swaying from side to side a substantial amount. The depth of the openings 508 will be illustrated more clearly in FIGS. 11 and 12.

In some embodiments, the substrate 504 includes one or more support members 704 that extend from the substrate 504 and provide support. In the embodiment of FIG. 7, the substrate 504 includes four support members 704, one at each corner of the substrate. However, these support members can be designed in various ways and there can be more than four or fewer than four, as suitable. The support members 704 provide support to the substrate 504, and can support the substrate 504 when resting on a surface, on a robotic instrument, in the base 506, or other locations. In some embodiments, the substrate 504 is designed to be a sufficient height that when the substrate 504 is loaded with optical assemblies 26 and set on a surface without the base 506 or container 602 below, the tips of the optical assemblies 26 will still not contact the surface or contact each other. The support members 704 allow the substrate 504 to be positioned on the base 506 by extending through slots in the base (see FIG. 8). The support members 704 can slide into the openings in the base 506 and the notches 706, 708 further contact the base to allow the substrate 504 to be securely positioned on the base 506.

In some embodiments, the support members 704 are designed to extend down into a robotic instrument platform or other device to locate the sensors with respect to the instrument robotics. The support members 704 can make contact with a mating surface in the instrument and provide datum surfaces for location during installation. Thus, any position tolerance increase that might have been contributed to by the base 506 is therefore avoided, since the base 506 does not need to be used for location in the instrument.

The substrate 504 illustrated in the embodiment of FIG. 7 also includes a raised edge 702 that surrounds the center surface of the substrate 504 and a recess 709 into which the optical assemblies 26 are placed. Thus, the optical assemblies can be positioned down into the recess 709 and can be protected by the edge 702. The edge 702 provides the sensors with some protection against getting knocked out of the openings 508 when the cover 502 is not in place. The recess 709 further provides some protection of the sensors when the cover 502 is in place, since the cover has a corresponding recess that helps to hold the sensors in position (see FIG. 9).

Figure 8:
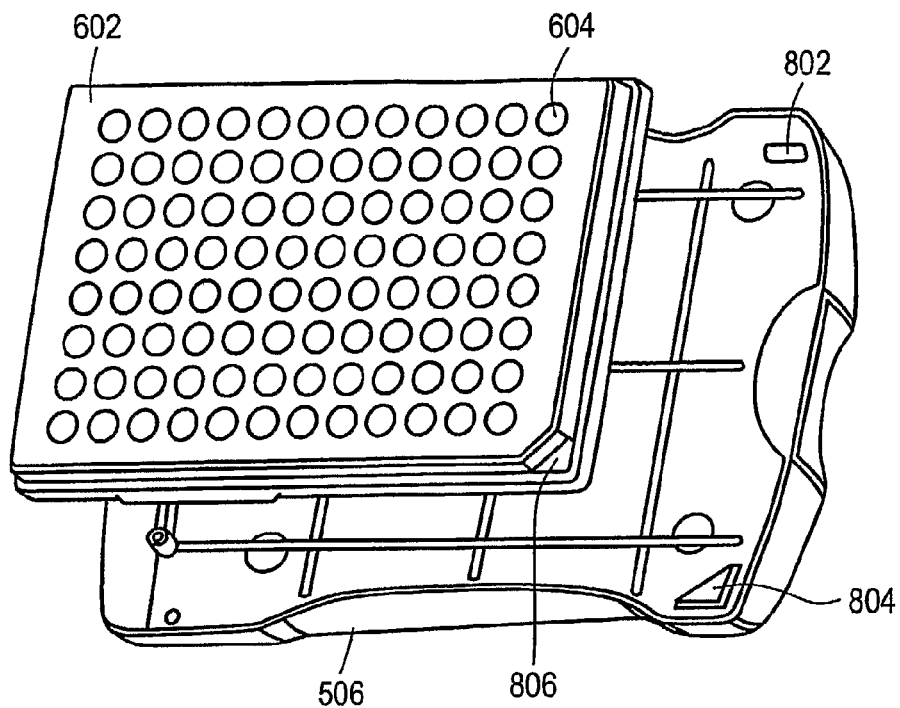
FIG. 8 shows an exploded view of the container of wells and a base structure, according to an embodiment.

FIG. 8 shows an exploded view of the base 506 and container 602, according to an embodiment of the invention. The container 602 can be placed in the base 506 so that the ends of the optical assemblies 26 are aligned with the wells 604 in the container 602. FIG. 8 also illustrates that container 602 can be removed from the base 506 and replaced as required. Where the container 602 is a standard microtiter plate, the used plate can easily be removed after use in pre-wetting or immobilization and replaced with a new, clean plate, as needed.

As described previously, the base 506 can include openings or slots 802 for placement of the substrate 504. In the embodiment of FIG. 8, there are four slots 802 in the base 506, one at each corner. As the substrate 504 is placed over the base 506, the substrate 504 is guided into position while preventing contact between the ends of the optical assemblies 26 and other surfaces. The support members 704 of the substrate 504 are guided into the slots 802 in the base to provide secure positioning of the substrate 504 in the base 506. The base 506 thus can protect the tips of the optical assemblies 26 when the substrate 504 is positioned on the base 506 without the container 602 in between. The base 506 can also assist in guiding the substrate 504 into place for the proper positioning of the optical assemblies 26 in the wells 604 when the substrate 504 is positioned on the base 506 over container 602.

In some embodiments, the base 506 also includes a mounting notch 804 that mates with the corner orientation notch 806 of the container 602. In this manner, the user can easily find the correct orientation of the container 602 in the base 506. The container 602 can be secured into position by sliding the orientation notch 806 under the mounting notch 804 to force the container 602 into its specified orientation.

Figure 9:
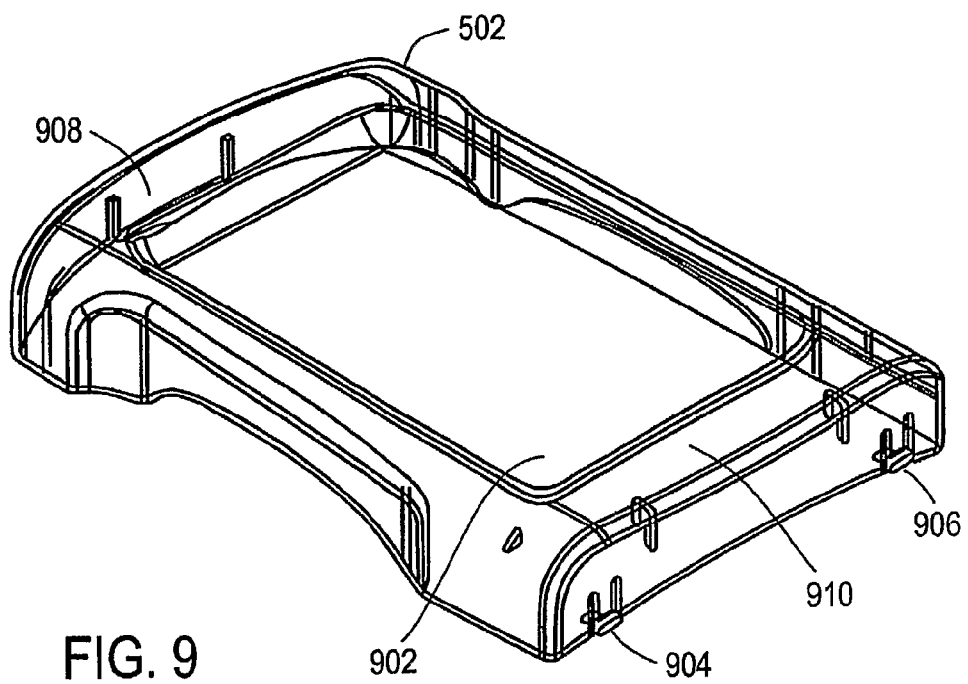
FIG. 9 shows a perspective view of the cover for the apparatus, according to an embodiment of the invention.

Referring now to FIG. 9, there is shown the cover 502 for the apparatus 500, according to an embodiment of the invention. The cover 502 can be generally contoured to fit the shape of the substrate, including a raised outer edge 910 around the periphery of the cover 502 and a recess 902 in the center of the cover 502. The cover 502 fits over the top of the substrate 504 and protects the hub 404 end of the optical sensing assembly 26 from environmental contamination or other damage. The cover 502 can be designed to fit such that the sensors cannot lift from the holes in the substrate 504, regardless of the position of the apparatus 500 in space. For example, in this embodiment, even if the apparatus 500 is held upside down, the cover will retain the sensors in position in the opening 508 of the substrate 504. One feature that allows the cover 502 to hold the optical assemblies 26 firmly in place is the recess 902 in the top of the cover. This recess 902 corresponds with the recess 709 in the substrate 504, and thus the center portion of the cover 502 extends down into the recess 709 of the substrate 504. In this manner, the center portion of the cover 502 is lowered close to the hubs 404 of the optical assemblies 26 when the assemblies 26 are positioned in the openings 508 of substrate 504 to maintain the assemblies 26 in the openings 508.

In some embodiments, the cover includes structures 904 and 906 that engage the base 506 to snap the cover 502 into position on the base 506. Various other types of locking mechanisms can be used, as well, for locking the cover to the base. In some embodiments, the cover 502 and the base 506 lock into the substrate 504 rather than locking into each other. In some embodiments, the cover 502 further includes flap 908 that engages a notched portion of the base 506 (that will be illustrated in FIG. 10), and provides a gripping means for the user to grip the cover 502 and separate the cover 502 from the apparatus 500. In addition, the recess 902 can also provide for nestled stacking of assemblies 500 during storage. The base 506 includes feet (that will be illustrated in FIG. 10) that will rest in the recess 902 when one apparatus is placed on top of another, thus securing the stacked configuration.

Figure 10:
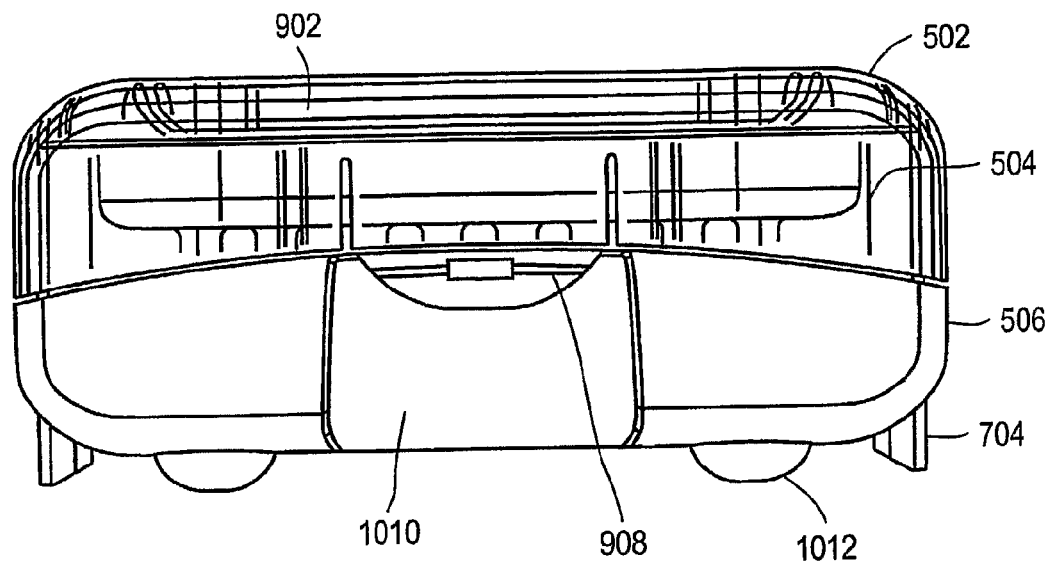
FIG. 10 shows a side view of the apparatus, according to an embodiment of the invention.

FIG. 10 shows a side view of the apparatus 500, according to an embodiment of the invention. FIG. 10 further illustrates the flap 908 of the cover 502, and how this flap 908 rests against notch 1010 in the base, according to an embodiment of the invention. The notch 1010 provides a space into which a user can slip his/her fingers to grip the flap 908 and remove the cover 502. In addition, FIG. 10 illustrates the stacking feet 1012 of base 506 that permit nestled stacking of assemblies 500, according to an embodiment. In this embodiment, the feet 1012 of one apparatus 500 can rest in the recess 902 of another apparatus 500, thus holding the two assemblies 500 in place during storage. The stacking feet 500 can also provide support for the apparatus 500 when the apparatus is resting on a surface. FIG. 10 further illustrates the support members 704 of substrate 504, and shows how these engage the base for secure fitting, according to an embodiment of the invention.

Figure 11:
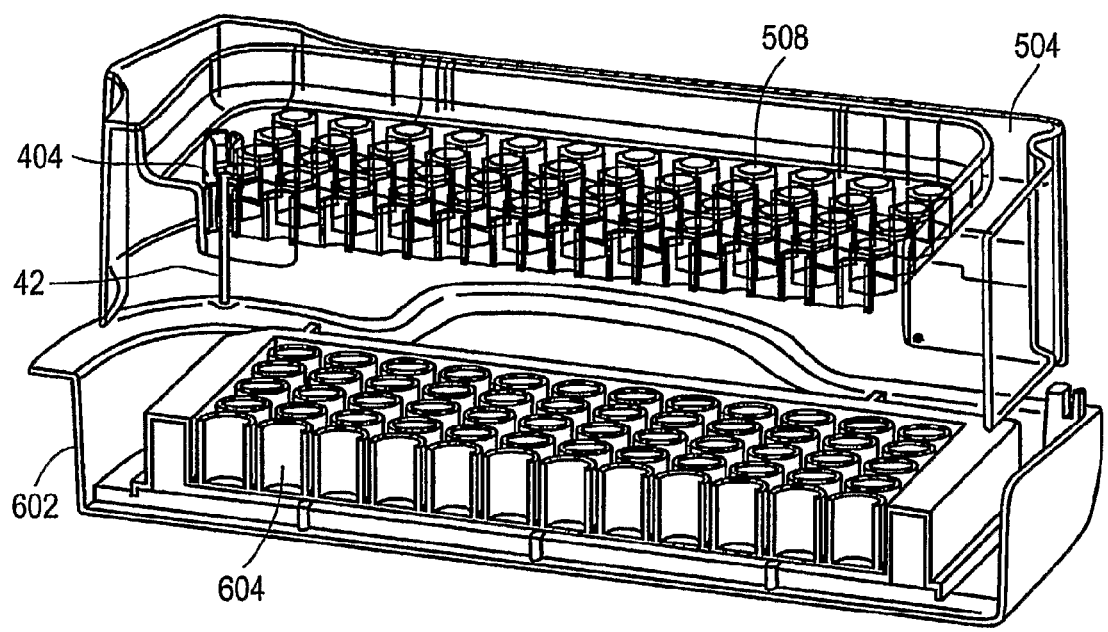
FIG. 11 shows a cross-section of a side view of the apparatus with the tip lined up with the well, according to a embodiment of the invention.

FIG. 11 shows a cross-sectional view of the side of the apparatus 500, including the substrate 504, the container 602, and the base 506, according to an embodiment of the invention. FIG. 11 illustrates how the hub 404 rests at the top of the substrate 504, and the fiber 42 is suspended below the substrate 504 from the opening 508, according to some embodiments. The optical sensing assembly 26 is positioned above one of the wells 604, and is positioned for insertion of the fiber 42 inside the well 604.

Figure 12:
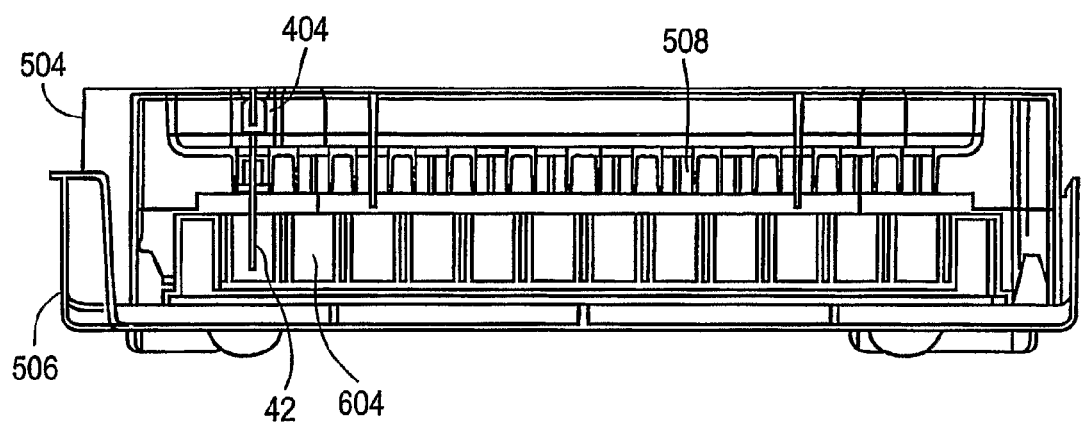
FIG. 12 shows a cross-section of a side view of the apparatus with the tip of the optical sensing assembly inside the well, according to an embodiment of the invention.

FIG. 12 further shows another cross-sectional view of the side of the apparatus 500, including the substrate 504, the container 602, and the base 506, according to an embodiment of the invention. This view shows the fiber 42 inside of a well 604 that can be filled with solution or sample. The optical sensing assembly 26 is positioned so that only a portion of the fiber is inside the well, and thus only a portion will contact the solution (however, this positioning can vary as needed). FIG. 12 further illustrates the length of the opening 508 in this embodiment. The opening 508 at the upper surface of the substrate 504 can have an elongated barrel below the surface that extends a distance beyond the surface of the substrate 504. This design can provide additional support for the optical sensing assembly 26 to avoid tipping or swaying of the optical sensing assembly 26 and to keep the assembly 26 from contacting other nearby assemblies 26 or other surfaces.

While the many of the embodiments shown herein include both a cover 502 and a base 506, these elements are optional. In some embodiments, either the cover 502 or base 506, or both, are excluded from the apparatus 500. In addition, the shape of the apparatus 500 can vary, as suitable.

Figure 13A:
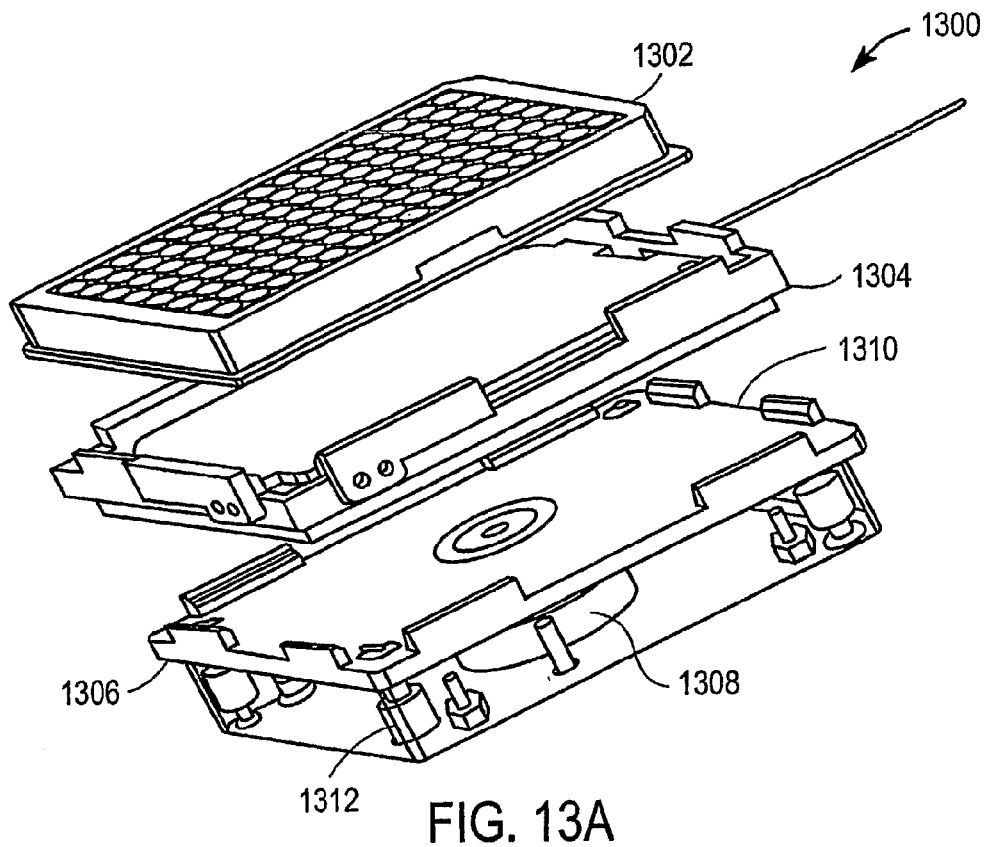
FIGS. 13a and b show an apparatus for agitation of solution in a well relative to an optical sensing assembly, according to an embodiment of the invention.
Figure 13B:
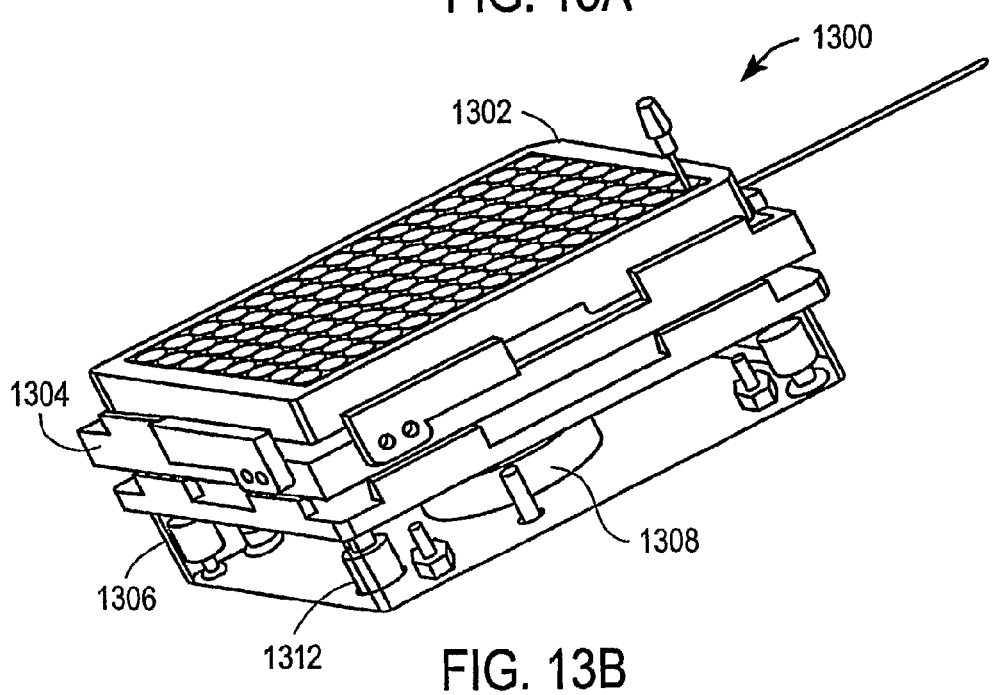
FIG. 13c shows a robotic instrument for assay, according to an embodiment of the invention.

Referring now to FIGS. 13a and 13b, there is shown illustrations of an orbital flow apparatus 1300, according to an embodiment of the present invention. The orbital flow apparatus 1300 can include a container 1302, an agitation assembly 1306, an agitation device 1306 and a heater adapter 1304. However, one or more of these parts can be left out of the apparatus or other parts can be added, as suitable for a given application. Instead of using a flow cell or microfluidics to create surface flow in a well, the invention disclosed herein describes a different manner for creating flow. The orbital flow apparatus 1300 shown in FIG. 13 provides a mechanism for creating the flow needed in a sample well of a container 1302 for a molecular binding kinetic analysis or movement of buffer solution in a well. Without proper flow, it is very difficult to measure the disassociation of molecules from the sensor surfaces. Container 1302 is similar to container 602, and thus it can be a 96-well microtiter plate as shown in FIGS. 13a and b, a 384-well or 1536-well microtiter plate, or some other type of container. The orbital flow mechanism allows for the exposure of a biosensor or optical sensing assembly 26 to a relatively large bulk of reagents. This apparatus 1300 can provide for continuous flow of reagent over an optical sensing assembly 26 by rotating the container 1302 to create orbital flow within the wells. FIG. 13b illustrates an optical sensing assembly 26 as was shown in FIGS. 1-12. This assembly 26 is suspended in a solution in the wells of container 1302. The apparatus 1300 is designed to create relative flow between the assembly 26 and the sample in which the biosensor is immersed by moving or rotating the container 1302 in a plane perpendicular to the optical assemblies 26, according to a specified type of motion (e.g., repetitive motion, random motion, etc.).

One embodiment of the apparatus 1300 uses a repetitive flow mechanism. In this embodiment, the mechanism creates a repetitive motion, resulting in relative movement of the assembly 26 and the sample in the well. This type of mechanism can be designed in a number of manners. One example is shown in FIG. 13 that includes a surface 1310, which can be a substantially flat surface that rests on suspensions 1312. In the example shown in FIG. 13, there are four flexible suspensions 1312, but any other type of mechanism can be used. The example shown in FIG. 13 further includes an agitation assembly 1306 with an agitation device 1308 (e.g., an electrical motor or another type of device for providing movement or agitation) that is positioned below the surface 1310 (or adjacent to the surface 1310). The agitation device 1308 includes a driving mechanism for the repetitive motion, in this embodiment. In the example illustrated in FIG. 13, the motor rotates the container 1302 in a plane that is perpendicular to the optical sensing assembly 26 to cause the agitation to occur. This movement of the motor causes the sample to move relative to the assembly 26, thus causing continuous flow of the sample over the biosensor surface. In some embodiments, the orbital motion can be controlled from 10 rpm to 5000 rpm. In other embodiments, the motion can be controlled from 1 rpm to 10,000 rpm, from 100 rpm to 2000 rpm.

Some embodiments of the apparatus 1300 include an actuator (e.g. electrical motor, piezo actuator, solenoids, etc.) to create a repetitive motion that is not in orbital trajectory. The possible trajectories can include linear, elliptical, sinusoidal, etc., or any combination of these motions in the three-dimensional space.

Another embodiment of the apparatus 1300 uses a random flow mechanism. In this embodiment, the mechanism generates a random motion or vibration that agitates the sample in the wells, and thus creates relative movement of sample against the biosensor surface 26. For example, an ultrasound source can be used to agitate the sample or solution to create flow of the sample over the biosensor 26.

In still other embodiments, instead of causing orbital movement of the solution inside the well relative to the optical assembly 26, the assembly 26 is agitated while the solution is kept substantially stable. An agitation assembly 1306 can be attached to the assembly to cause the assembly 26 to move relative to the sample, thus creating relative movement of the sample over the biosensor. Additionally, both the solution and the optical assembly 26 can be agitated in some embodiments.

In addition, movement of either the optical assembly 26 or the sample is not limited to circular or elliptical motion. Agitation can be created using numerous other types of motion, such as movement up and down (i.e., by moving the sample up and down or the biosensor up and down), movement in a straight line, vibrational movement, etc.

In some embodiments, the agitation assembly 1306 includes a heater adapter 1304 that connects to the container 1302 and the agitation assembly 1306 by being sandwiched in between the two. The heater adapter 1304 is mounted onto the orbital flow device to provide heated flow during binding measurements. FIG. 13 shows how the pieces of apparatus 1300 fit together, and can lock into place.

Figure 13C:
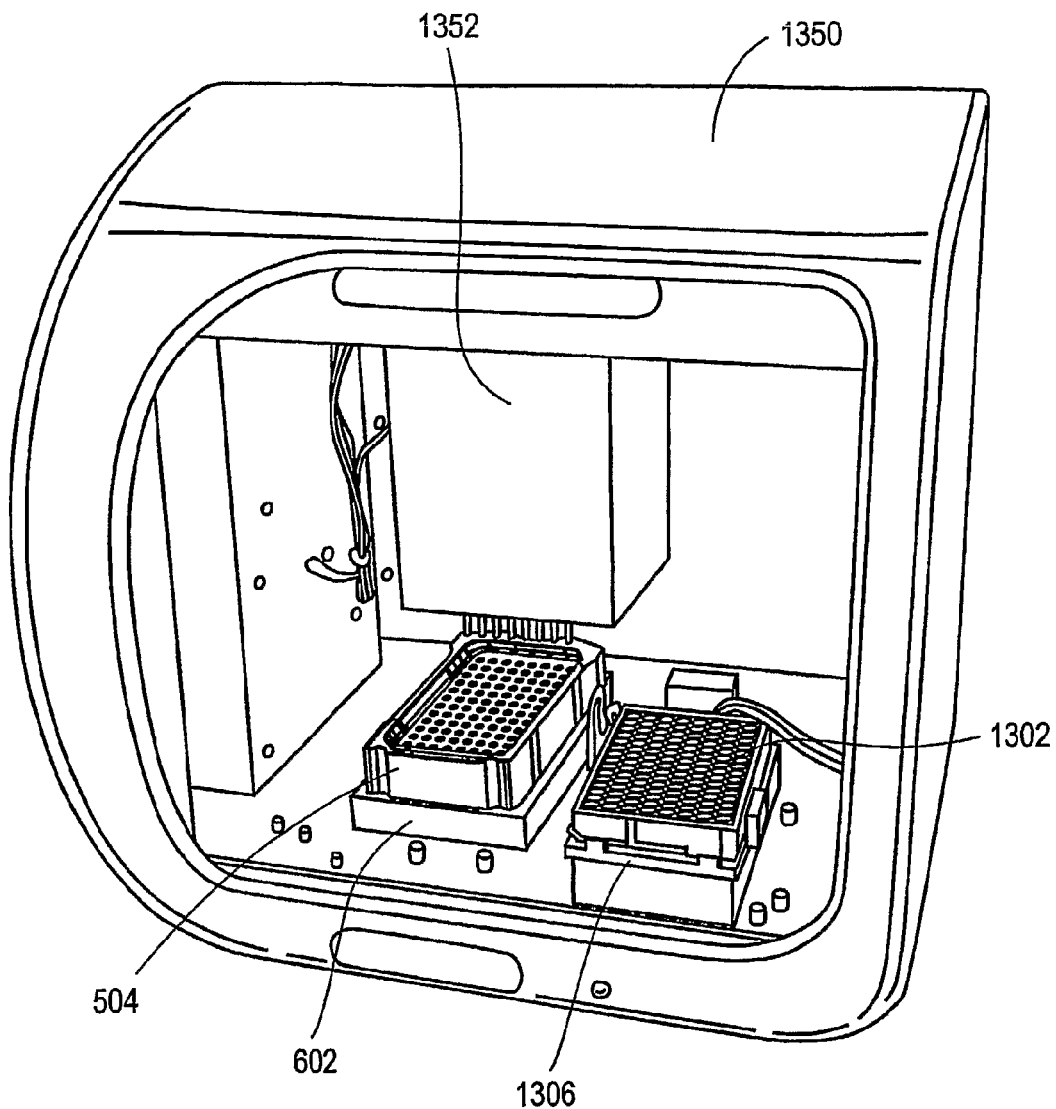

As described above, the orbital flow apparatus 1300 can be included in a robotic instrument for assay. FIG. 13c better illustrates this usage of the inventions described herein in a robotic instrument for assay. Robotic instrument 1350 is shown in FIG. 13c, and this instrument can be included as a part of interferometer system 20, described above. In some embodiments, container 1302 can be mounted to the agitation assembly 1306 and can contain samples to be tested during assay (e.g., the second microtiter plate referred to above). The container 1302 can be mounted alongside substrate 504 that is holding optical assemblies 26. A robotic arm 1352 can transfer one or more of the assemblies 26 from the substrate 504 over to the container 1302 and can dip the assemblies 26 into the samples in the wells of container 1302. The agitation assembly 1306 causes agitation of the container 1302 while the tips of the assemblies 26 are dipped into the samples, thus creating flow of the sample over the optical assemblies 26 for kinetic analyses or other types of assays.

The following example illustrates a method of the invention for creating orbital flow, but is in no way intended to limit its scope.

EXAMPLES

Below is an example of a specific embodiment for carrying out the present invention. The example is offered for illustrative purposes only, and is not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Multi-concentration Kinetic Experiment with Direct Comparison of Flow=0 and Flow=140 rpm.

This example demonstrates the creation of orbital flow of a sample relative to the biosensor. In this example, a set of biosensors was coated with an antibody against mouse IgG2b.

Figure 14:
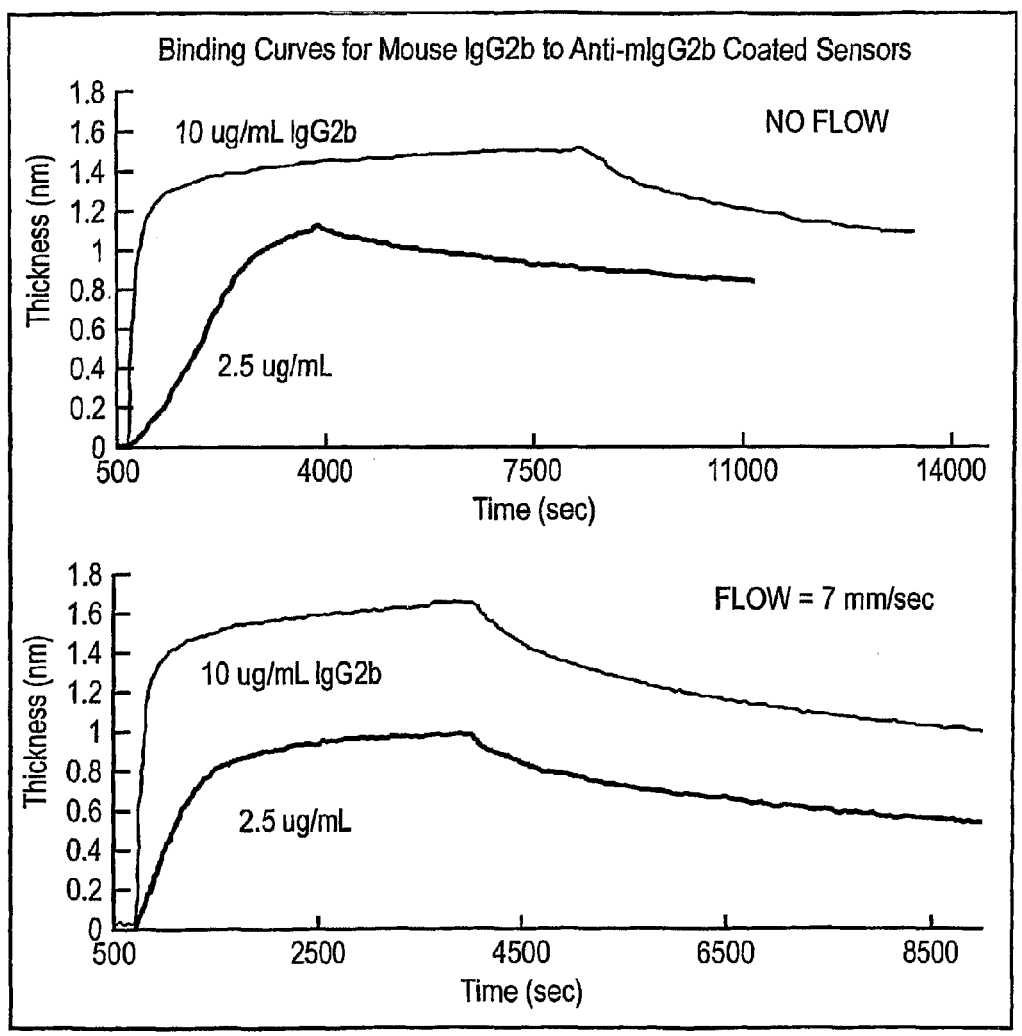
FIG. 14 shows a graphical illustration of binding curves with and without flow, according to an embodiment of the invention.

The analyte (mouse IgG2b) was added into an assay buffer (1 mg/mL bovine serum albumin in phosphate buffered saline, 0.02% Tween-20) at the concentration specified in FIG. 14. FIG. 14 shows, in two graphs, the binding curves for the mouse IgG2b to the Anti-mouse IgG2b-coated sensors where flow is equal to 0 (e.g., no flow; depicted in the upper graph) and where flow is equal to 7 mm/sec (depicted in the lower graph). Binding of the analyte to the antibody was monitored using the technique of Biolayer Interferometry, and binding was recorded as a nanometer (nm) increase in thickness of the binding layer (i.e., the layer formed by binding of the analyte to the anti-analyte) as a function of time (in seconds). The graphs show that the orbital flow (i.e., where flow=7) eliminates the early "lag" phase of binding of a 2.5 ug/ml sample of mouse IgG2b to the coated sensor due to diffusional barriers (i.e., which can be seen where flow=0). Therefore, the apparatus 1300 for creating orbital flow allows for flow of the sample over the biosensor resulting in binding without the "lag" phase that occurs when the apparaus 1300 is not used to create orbital flow.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. An apparatus for packaging an optical sensing assembly, the apparatus comprising at least one discrete optical sensing assembly comprising an optical fiber and a transparent optical element having end faces and first and second reflecting surfaces formed on the end faces, the first and second reflecting surfaces separated by at least 50 nm, wherein the first reflecting surface comprises a layer of analyte binding molecules; a substrate with a plurality of openings, each opening being configured for holding a discrete optical sensing assembly therein, the optical sensing assembly being positioned in the opening with a tip of the optical sensing assembly extending through the opening to be suspended from the substrate, wherein the plurality of openings are arranged so the optical sensing assembly positioned therein avoids contacting another optical sensing assembly positioned therein, and wherein at least one opening holds an optical sensing assembly therein, with the tip of the optical sensing assembly extending through the opening.

2. The apparatus of claim 1, further comprising a support member for supporting the substrate, the support member positioning the substrate so the tip of the optical sensing assembly suspended from the opening in the substrate contacts a solution in one of a plurality of wells in a container adjacent to the substrate.

3. The apparatus of claim 2, wherein the container is a microtiter plate including 96 wells.

4. The apparatus of claim 2, wherein the optical sensing assembly in the substrate is mapped to wells in a second container containing different samples.

5. The apparatus of claim 2, wherein the solution is a pre-wet solution into which the optical sensing assembly is immersed.

6. The apparatus of claim 2, wherein the solution is a protein solution into which the optical sensing assembly is immersed for immobilization of protein on the optical sensing assembly, or for measurement of interaction with another protein already immobilized on the optical sensing assembly.

7. The apparatus of claim 2, wherein the substrate being configured for preparing the optical sensing assembly for assay further comprises the substrate being configured for pre-wet of the optical assembly before assay.

8. The apparatus of claim 2, wherein the substrate being configured for preparing the optical sensing assembly for assay further comprises the substrate being configured protein immobilization of the optical assembly before assay.

9. The apparatus of claim 1, wherein the optical sensing assembly further comprises a hub at an end of the assembly opposite the tip, the hub being designed for attachment to a device that moves the assembly from a first location to a second location.

10. The apparatus of claim 1, wherein the openings include elongated barrels that allow the optical sensing assembly to be immersed in a solution in a container below the substrate without the tip of the optical sensing assembly contacting a tip of another optical sensing assembly in the substrate.

11. The apparatus of claim 1, comprising a plurality of discrete optical sensing assemblies coated with different reagents arranged in the plurality of openings.

12. The apparatus of claim 1, wherein the at least one optical sensing assembly comprises a hub at an end opposite the tip, and the optical sensing assembly is inserted into the opening with the hub of the assembly remaining on a first side of the substrate and the tip of the assembly being inserted through the opening to be suspended from a second side of the substrate.

13. The apparatus of claim 1, further comprising a cover on a first side of the substrate to protect the optical sensing assembly.

14. The apparatus of claim 13, wherein the cover comprises a recess comprising a downwardly extending center portion such that, when the cover is closed over the substrate, the cover retains the optical sensing assembly in the opening in position in the substrate.

15. The apparatus of claim 14, further comprising a cover and a base, the cover and base being designed to lock together around the substrate forming an enclosure around the optical sensing assembly.

16. The apparatus of claim 15, wherein the base of the apparatus is designed fit together with the cover of other apparatuses to be stackable with the other apparatuses for storage.

17. The apparatus of claim 14, further comprising a support member for supporting the substrate, the support member positioning the substrate so the tip of the optical sensing assembly suspended from the opening in the substrate can contact a solution in one of a plurality of wells in a container adjacent to the substrate, wherein the container is a microtiter plate.

18. The apparatus of claim 1, further comprising a base on a second side of the substrate to protect the tip of the optical sensing assembly.

19. The apparatus of claim 18, wherein a container is positioned inside the base beneath the substrate, the container being positioned so the tip of the suspended optical sensing assembly contacts solution in one of the plurality of wells in the container.

* * * * *